(12) United States Patent
Hammond et al.

(10) Patent No.: US 12,650,421 B2
(45) Date of Patent: Jun. 9, 2026

(54) FLUIDIC IMAGING BARRIER, COLLECTION CONTAINER AND METHOD OF USING SAME FOR SEPARATING AND IMAGING COMPONENTS OF A SAMPLE FLUID

(71) Applicant: IDEXX Laboratories, Inc., Westbrook, ME (US)

(72) Inventors: Jeremy Hammond, Standish, ME (US); Jui Ming Lin, Falmouth, ME (US); Timothy Butcher, Windham, ME (US); Aravind Reghu, Scarborough, ME (US)

(73) Assignee: IDEXX LABORATORIES, INC, Westbrook, ME (US)

( * ) Notice: Subject to any disclaimer, the term of this patent is extended or adjusted under 35 U.S.C. 154(b) by 444 days.

(21) Appl. No.: 18/109,973

(22) Filed: Feb. 15, 2023

(65) Prior Publication Data

US 2023/0266296 A1     Aug. 24, 2023

Related U.S. Application Data

(60) Provisional application No. 63/312,542, filed on Feb. 22, 2022.

(51) Int. Cl.
*G01N 33/487*     (2006.01)
*G02B 21/34*     (2006.01)

(52) U.S. Cl.
CPC ....... *G01N 33/48735* (2013.01); *G02B 21/34* (2013.01)

(58) Field of Classification Search
CPC . G01N 33/48735; G01N 33/491; G02B 21/34
See application file for complete search history.

(56) References Cited

U.S. PATENT DOCUMENTS

| | | | | |
|---|---|---|---|---|
| 4,473,530 A | * | 9/1984 | Villa-Real | B01L 3/50825 |
| | | | | 73/863.52 |
| D681,843 S | | 5/2013 | Németh | D24/224 |
| 2019/0145973 A1 | * | 5/2019 | Slusarewicz | G01N 33/5308 |
| | | | | 435/283.1 |
| 2020/0238201 A1 | * | 7/2020 | Minagawa | G01N 33/5094 |
| 2022/0000456 A1 | | 1/2022 | Griffin et al. | |

* cited by examiner

*Primary Examiner* — Dirk R Bass

(74) *Attorney, Agent, or Firm* — McDonnell Boehnen Hulbert & Berghoff LLP

(57)     ABSTRACT

A collection container for separating and collection particles suspended in a sample fluid added to the collection container includes at least one barrier-forming fluid which is immiscible relative to the sample fluid and which has a specific gravity which is different from the specific gravity of the sample fluid. The barrier-forming fluid is situated in the collection container to be in contact with the sample fluid and to form with the sample fluid a fluidic imaging barrier at the interface between the sample fluid and the barrier-forming fluid. The particles suspended in the sample fluid will separate therefrom when centrifugal or gravitational forces are applied to the container and will collect at the fluidic imaging barrier for imaging by an optical imaging system.

10 Claims, 13 Drawing Sheets

26
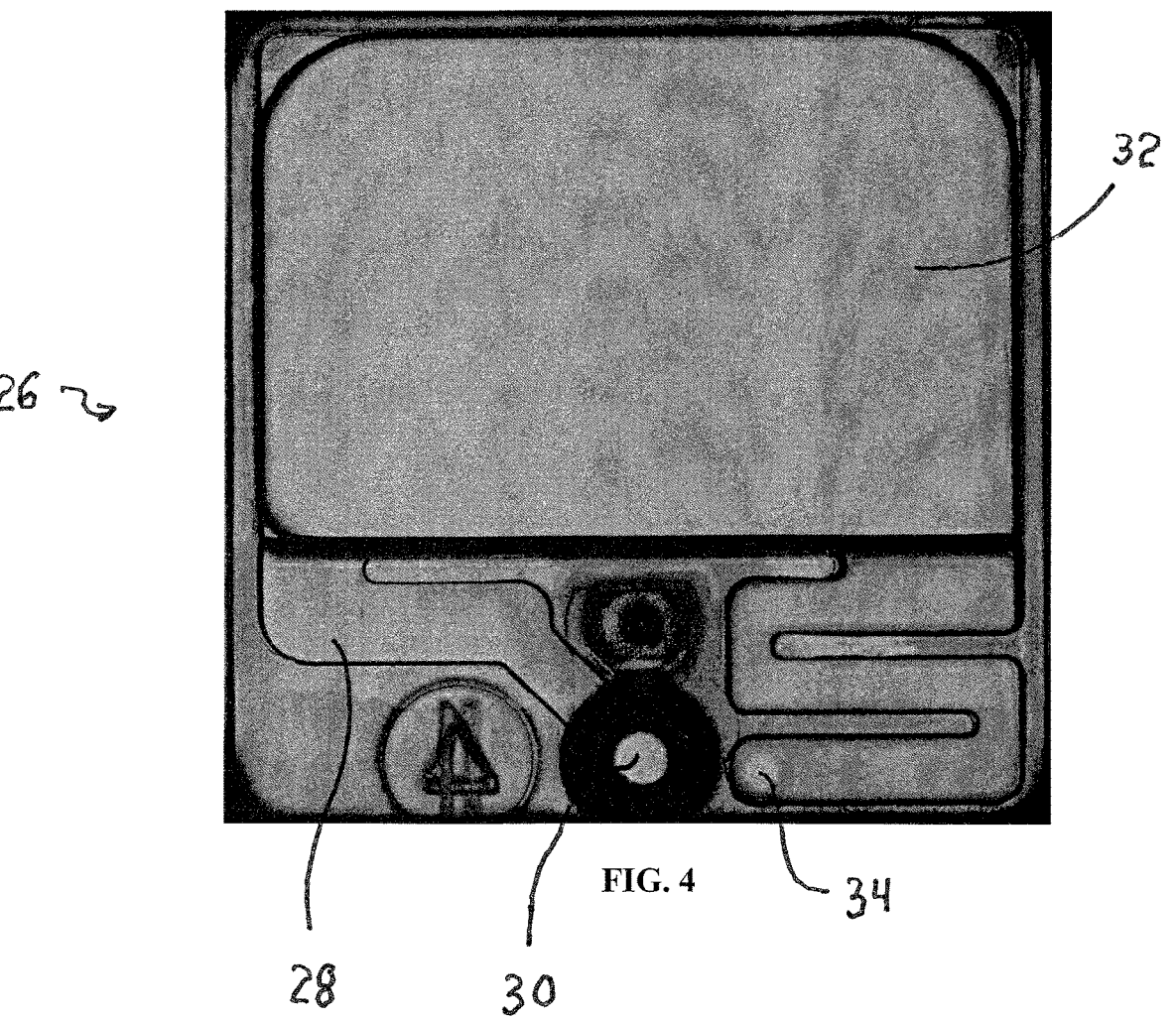
32
28    30    FIG. 4    34

FLUIDIC IMAGING BARRIER, COLLECTION CONTAINER AND METHOD OF USING SAME FOR SEPARATING AND IMAGING COMPONENTS OF A SAMPLE FLUID

CROSS-REFERENCE TO RELATED APPLICATIONS

This application is related to U.S. Provisional Patent Application Ser. No. 63/312,542, filed on Feb. 22, 2022, and titled "Fluidic Imaging Barrier, Collection Container And Method Of Using Same For Separating And Imaging Components Of A Sample Fluid", the disclosure of which is hereby incorporated by reference and on which priority is hereby claimed.

BACKGROUND OF THE DISCLOSURE

Field of the Disclosure

The present disclosure generally relates to devices and methods for separating components of a sample fluid, and more specifically relates to devices and methods for separating such components and concentrating the separated components to facilitate the imaging of such concentrated, separated components or the extraction thereof from the sample fluid.

Description of the Related Art

It is well known to use gravity and buoyancy as fundamental scientific principles that can be exploited in scientific and engineering designs. An example of such is the common practice in the healthcare industry to use a centrifuge on a microcentrifuge tube filled with whole blood to determine the Packed Cell Volume (PCV), or what proportion of the whole blood is red blood cells (RBCs). An alternative medical example would be using flotation fluids with defined specific gravities so that ova shed in fecal samples will float to the top of the fluid to be captured on a microscope cover slip such that such captured ova may be analyzed microscopically on a slide.

For further examples of methods and devices using flotation (i.e., buoyant forces) or centrifugation for separating particles in a liquid sample, reference should be had to U.S. patent application Ser. No. 17/363,279, filed on Jun. 30, 2021, which is titled "Collection Device and Method", naming IDEXX Laboratories, Inc. as the applicant, the disclosure of which is incorporated herein by reference.

These are but a few of many examples of using gravity, buoyancy or centrifugation to help separate particles in a sample fluid, but the common approach remains the same; that is, by either waiting for gravity or buoyancy to separate materials in a fluid medium or by using centrifugation to speed up the process, one can effectively concentrate elements of interest for later imaging and analysis.

When a diagnostic solution for a sample fluid includes microscopy of the solid elements within the sample using an optical imaging system, it can help the method if the solid elements are located in a small portion of the container. Common approaches include sedimentation, where the solid elements are either allowed to settle by gravity or encouraged to settle with an applied force, such as by centrifugation. The imaging system now gains the benefit of the entire fluid volume concentration of solid elements all in a single focal plane at the bottom of the container. The image scanning can now proceed with scanning only that plane in which the settled particles reside and gaining the benefit of such concentration of particles within the larger volume of sample occupying the depth of the container.

An alternative approach could be to allow the solid elements to float to the top of the container (depending on the fluid characteristics and those of the solid elements) and then scan the top surface of the container instead of the bottom. Implementation hurdles can still arise if the surface where the solid elements reside is too large, resulting in excessively long scan times, large data storage and long evaluation times. In these cases, it can be beneficial to design the container so that the scan area in which the solid elements reside is made small enough to address the aforementioned implementation constraints, although this, too, may lead to other problems if the fluid volume must be maintained and the depth of the fluid in the container is relatively large, requiring more time or effort to get the solid elements to sink or float, and can cause difficulties for standard microscopy approaches, where light is provided on one side of the fluid and imaging occurs on the other side, such as shown in FIGS. 1A and 1B for a standard and inverted microscopy instrument.

More specifically, FIG. 1A shows in a simplified form an optical imaging system 2 in a standard configuration in which a camera 4 or light detector is situated above a container 6 holding a sample fluid, and a light source 8, such as one or more light emitting diodes (LEDs), is situated below the sample container 6 to illuminate the container 6 from below. FIG. 1B shows in a simplified form an optical imaging system 2 in an inverted configuration in which a camera 4 or light detector is situated below a container 6 holding a sample fluid, and a light source 8, such as one or more LEDs, is situated above the sample container 6 to illuminate the container 6 from above.

With an extended path length for imaging and the additional potential for scattering or absorbance due to an increased fluid volume, there are physical limitations to the geometry of a container 2 holding a fluid and used for imaging solid elements in the fluid.

Beyond allowing solid elements to float or sink in the sample fluid, lateral forces can be applied to the sample fluid, driving the solid elements to one side of the container 2. An example of such using centrifugation is shown in FIG. 2. Lateral forces can be applied actively by centrifugation or other means, or passively by the vertical orientation of the container 2 and allowing gravitational forces or flotational forces to move the solid elements. The container 2 has physical boundaries, such as a bottom wall and side walls, where the lateral forces cannot further push the solid elements, and such boundaries provide a prescribed location at which the separated solid elements collect for imaging.

However, there are often benefits of keeping solid elements to be imaged away from solid boundaries, as those edges or walls can provide optical interference when evaluating the morphology or structure of the solid elements within the fluid. For example, injection molded thermoplastic containers may have welding debris, imperfections, marring, or other defects or artifacts on the container's inner surfaces which interfere with accurate imaging of micronsize elements or particles.

OBJECTS AND SUMMARY OF THE DISCLOSURE

It is an object of the present disclosure to provide a container having at least one fluidic barrier at which particles suspended in a fluid received by the container may collect.

It is another object of the present disclosure to provide a fluidic barrier between two mutually immiscible fluids such that particles suspended in one of the fluids may collect at the fluidic barrier to facilitate imaging of the particles collecting thereat.

It is still another object of the present disclosure to provide a method of forming a fluidic, particle-collecting barrier in a container to facilitate imaging of particles carried by a fluid received by the container and collecting at the fluidic barrier.

It is yet another object of the present disclosure to provide a container in which particles separating from a fluid received by the container will collect in the container at a location therein spaced apart from the side walls, bottom wall and other physical boundaries of the container.

It is another object of the present disclosure to provide a container used for imaging particles carried by a fluid received by the container such that the particles, when separated from the fluid, will collect at a fluidic imaging barrier situated at a location in the container away from the side walls and bottom wall of the container, which container walls may have otherwise adversely affected the imaging of the collected particles.

It is still another object of the present disclosure to provide a fluidic barrier in a container and at which particles carried by a fluid received by the container may collect and be imaged such that the required number of images of the particles collecting at the fluidic barrier is minimized.

It is yet another object of the present disclosure to provide a container used for separating and collecting particles of a fluid received by the container which overcomes the inherent disadvantages of known fluid containers.

In accordance with one form of the present disclosure, a fluidic imaging barrier is formed between two mutually immiscible fluids having different specific gravities. Particles suspended in one of the fluids, or in a different fluid, separate from the fluid under the influence of gravity, centrifugation or flotation and collect at a location in proximity to the fluidic barrier where they may be more readily imaged by an optical imaging system.

In another form of the present disclosure, a fluidic imaging barrier is formed between a first fluid and a second fluid. The first fluid and the second fluid are immiscible relative to each other. The first fluid has a first specific gravity, and the second fluid has a second specific gravity. The first specific gravity of the first fluid is different from the second specific gravity of the second fluid.

In still another form of the present disclosure, at least a first fluidic imaging barrier and a second fluidic imaging barrier are provided. The first fluidic imaging barrier is formed between a first fluid and a second fluid. The second fluidic imaging barrier is formed between the second fluid and a third fluid. The first fluid is immiscible with respect to the second fluid. The second fluid is immiscible with respect to the third fluid. The first fluid has a first specific gravity. The second fluid has a second specific gravity. The third fluid has a third specific gravity. The first specific gravity of the first fluid is different from the second specific gravity of the second fluid and may be different from the third specific gravity of the third fluid. The second specific gravity of the second fluid is different from the third specific gravity of the third fluid.

In yet another form of the present disclosure, a container for holding a first fluid having particles suspended therein and for separating the particles from the first fluid so that the separated particles may be imaged by an optical imaging system includes container walls that define an interior cavity in which the first fluid having the suspended particles may be received. A second fluid is also received by the interior cavity of the container. The second fluid is immiscible with respect to the first fluid. The first fluid has a first specific gravity. The second fluid has a second specific gravity. Each of the particles of interest of the first fluid has a third specific gravity. The first specific gravity of the first fluid is different from the second specific gravity of the second fluid. The third specific gravity of the particles of the first fluid is different from the first specific gravity of the first fluid and the second specific gravity of the second fluid. The first fluid resides in a first location within the interior cavity of the container. The second fluid resides in a second location within the interior cavity of the container due to the second fluid being immiscible with respect to the first fluid and due to the second specific gravity of the second fluid being different from the first specific gravity of the first fluid. The first fluid residing at the first location within the interior cavity of the container is adjacent to and in fluidic contact with the second fluid residing at the second location along an interface between the first fluid and the second fluid and thereby defining a fluidic imaging barrier at the interface between the first fluid and the second fluid. The fluidic imaging barrier prevents particles which have separated from the first fluid from passing therethrough from the first fluid to the second fluid. The particles which have separated from the first fluid will collect at or near the fluidic imaging barrier such that the particles collecting thereat may be imaged by the optical imaging system.

Still another form of the present disclosure relates to a method of separating and collecting particles in a particle collection container, the container being configured with an interior cavity to hold a first fluid having particles suspended therein. More specifically, the collection container is used for separating the particles from the first fluid so that the separated particles may collect at a predefined area within the interior cavity of the container. In accordance with one form, the method includes the steps of adding the first fluid containing the suspended particles to the interior cavity of the container, and adding at least a second fluid to the interior cavity of the container either before or after the first fluid is added to the container. The at least second fluid added to the interior cavity of the container is immiscible with respect to the first fluid. The first fluid has a first specific gravity. The second fluid has a second specific gravity. The particles of the first fluid have third specific gravities. The first specific gravity of the first fluid is different from the second specific gravity of the second fluid. The third specific gravities of the particles of the first fluid are different from the first specific gravity of the first fluid and the second specific gravity of the second fluid.

The method includes the step of forming a fluidic imaging barrier between the first fluid and the second fluid. Because the second fluid is immiscible with respect to the first fluid and because the second specific gravity of the second fluid is different from the first specific gravity of the first fluid, the first fluid will be caused to reside in a first location within the interior cavity of the container, and the second fluid will be caused to reside in a second location within the interior cavity of the container. The first fluid residing at the first location within the interior cavity of the container is adjacent to and in fluidic contact with the second fluid residing at the second location along an interface between the first fluid and the second fluid, thereby defining a fluidic imaging barrier at the interface between the first fluid and the second fluid. The first fluid and the second fluid may be caused to move respectively to the first location and the second location within the interior cavity of the container either actively, for example, by centrifuging the container, or passively, such as by allowing gravity and/or flotation to act on the first fluid and the second fluid for a sufficient period of time to allow the first fluid and the second fluid to separate into their respective first and second locations within the interior cavity of the container and to define the fluidic imaging barrier at the interface between the first fluid and the second fluid.

The method includes the step of causing the particles suspended in the first fluid to separate from the first fluid to provide separated particles. The particles may be separated from the first fluid either actively, by centrifuging the container, or passively, by allowing gravity or flotation to act on the particles for a predetermined period of time.

The method includes the step of collecting the separated particles at or near the fluidic imaging barrier. Because the third specific gravities of the particles are different from the first specific gravity of the first fluid and the second specific gravity of the second fluid, the separated particles will move toward the fluidic imaging barrier formed at the interface between the first fluid and the second fluid such that the particles will collect at or near the fluidic imaging barrier. The fluidic imaging barrier prevents the particles which have separated from the first fluid from passing therethrough from the first fluid to the second fluid. The particles collecting at or near the fluidic imaging barrier may be imaged by an optical imaging system.

These and other objects, features and advantages of the present disclosure will be apparent from the following detailed description of illustrative embodiments thereof, which is to be read in connection with the accompanying drawings.

BRIEF DESCRIPTION OF THE DRAWINGS

FIG. 4 is a stitched image taken by a scanning microscope of a conventional fluid container in which one or more fluidic imaging barriers may be formed.

DETAILED DESCRIPTION OF THE PREFERRED EMBODIMENTS

The general approach of utilizing the specific gravities of immiscible fluids that will naturally remain separate from each other, like oil and water, to support optical diagnostics of solid elements suspended in one of the fluids is described herein. Judicious choice of fluids will help separate solid elements (also referred to herein as "particles") within the sample fluid at one of the fluidic interfaces, depending on the specific gravity of each fluid and those of the solid elements suspended in the sample fluid and the amount of time and/or force applied to the container holding the fluids for the solid elements, separated from the sample fluid, to reach a state of equilibrium. Given an appropriate container architecture, one can then design specifically where the solid elements will concentrate within that container, thereby providing an amplification approach for the optical scanning process that would otherwise require scanning over a significant number of images, costing time and computing power, and adding complexity to the scanning platform. The described approach will result in a known location for the solid elements to reside at equilibrium, thereby providing a faster means to identify the particles of interest and with fewer images. An expanded approach can utilize multiple fluids to create physical separation of different particles by their density to be in individual locations within a sample collection container for imaging.

As mentioned previously, it is preferred when imaging solid elements in a collection container to maintain the solid elements away from solid boundaries, such as the side walls and bottom wall of the container, as such walls may exhibit imperfections and other artifacts which may result in optical interference when evaluating the morphology or structure of the solid elements within a sample fluid. The collection container and method of the present disclosure overcome this problem by providing a physical stop for the migration of the solid elements, that is, by including one or more fluidic barriers at the interfaces between immiscible fluids at which the separated solid elements may collect away from the walls of the container.

Figure 3:
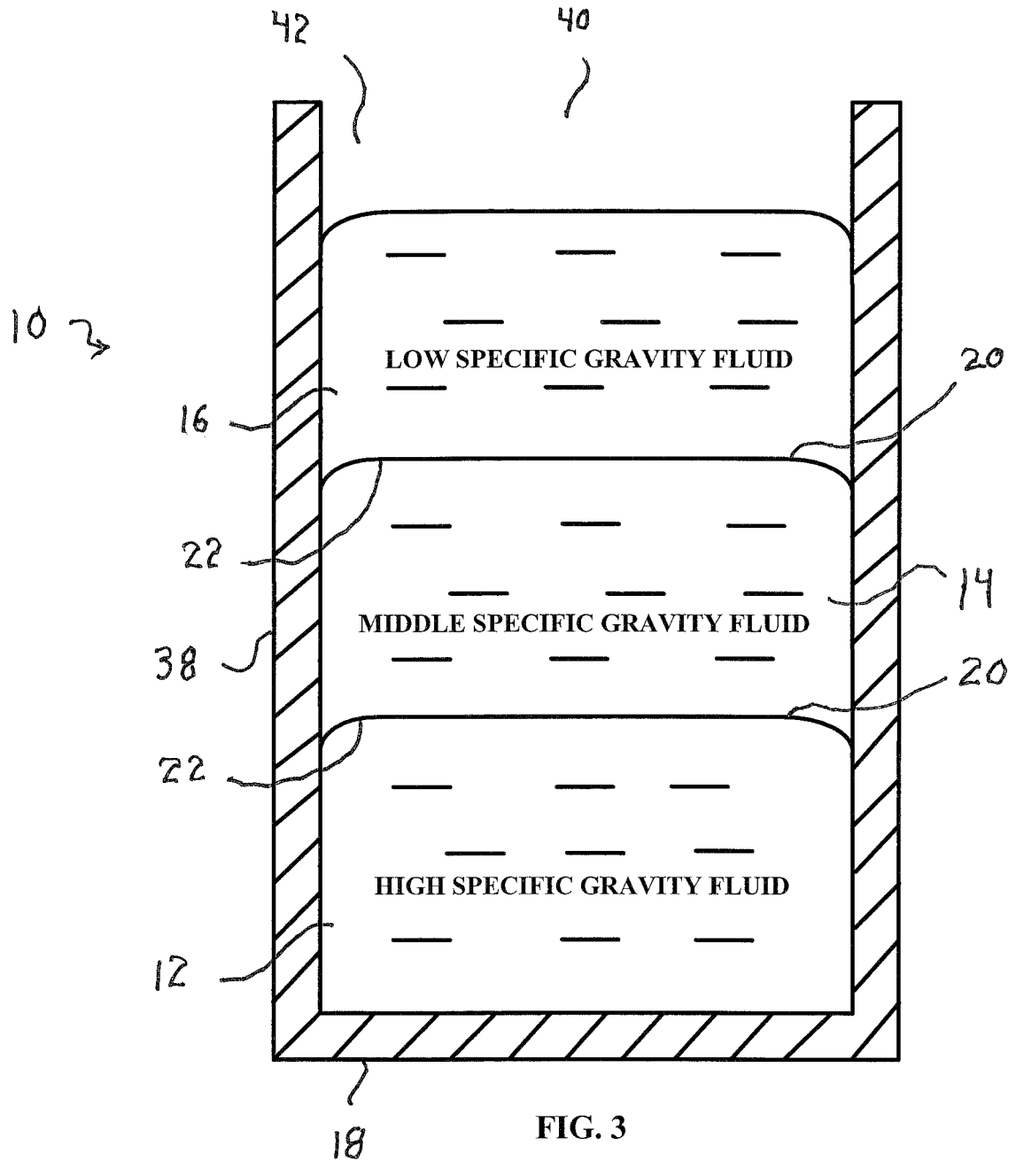
FIG. 3 is a simplified, longitudinal cross-sectional view of a container formed in accordance with the present disclosure for separating particles suspended in a fluid, the container holding three immiscible fluids which define fluidic imaging barriers at the interfaces between adjacent fluids.

Given a fluid container 10, the orientation of the container 10 and the composition of fluid within the container 10 will define where the fluid resides at equilibrium within the container 10. As shown in FIG. 3 of the drawings, if the total fluid within the container 10 includes two or more immiscible fluids 12, 14, 16, then the fluids will naturally settle within the container 10 due to gravity with the highest specific gravity fluid 12 at the bottom 18 of the container 10 and with successively lower specific gravity fluids 14, 16 disposed in decreasing order thereabove. Each interface 20 between adjacent fluids 12, 14, 16 of different specific gravities then provides a predictable interface that can be mathematically determined based on the volume of each fluid 12, 14, 16 in the container 10 and the geometry of the container 10, as illustrated by FIG. 3 of the drawings. At each interface 20 between adjacent immiscible fluids 12, 14, 16 having different specific gravities is formed a fluidic imaging barrier 22 at or near which solid elements of interest, separated from a sample fluid, may collect in a concentrated volume for imaging by an optical imaging system 2.

Stated another way, solid elements that may be present in the sample fluid (for example, fluid 12 shown in FIG. 3) will then act similarly based on their physical properties, including geometry and specific gravity (i.e., density). If the solid elements in the sample fluid 12 have appropriate specific gravities, then they will concentrate at one or more fluidic imaging barriers 22 formed as the interfaces 20 between the fluids 12, 14, 16.

Figures 1A, 1B:
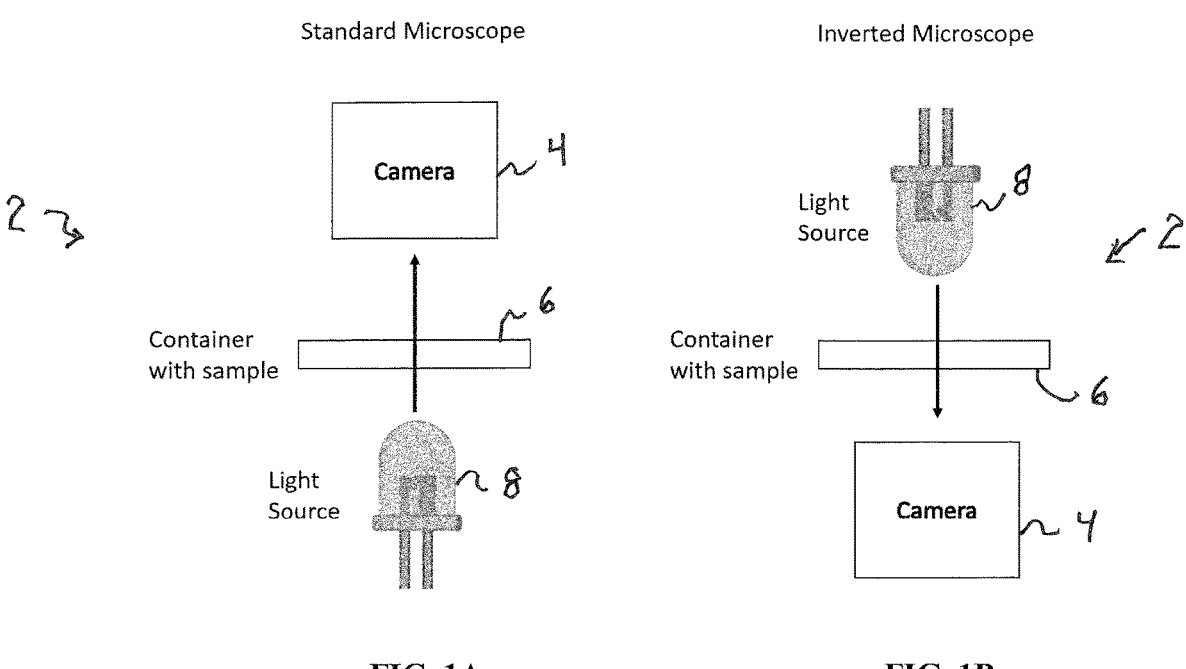
FIG. 1A is a simplified diagrammatic view of a standard microscopy light and optics configuration.
FIG. 1B is a simplified diagrammatic view of an inverted microscopy light and optics configuration.
Figure 10:
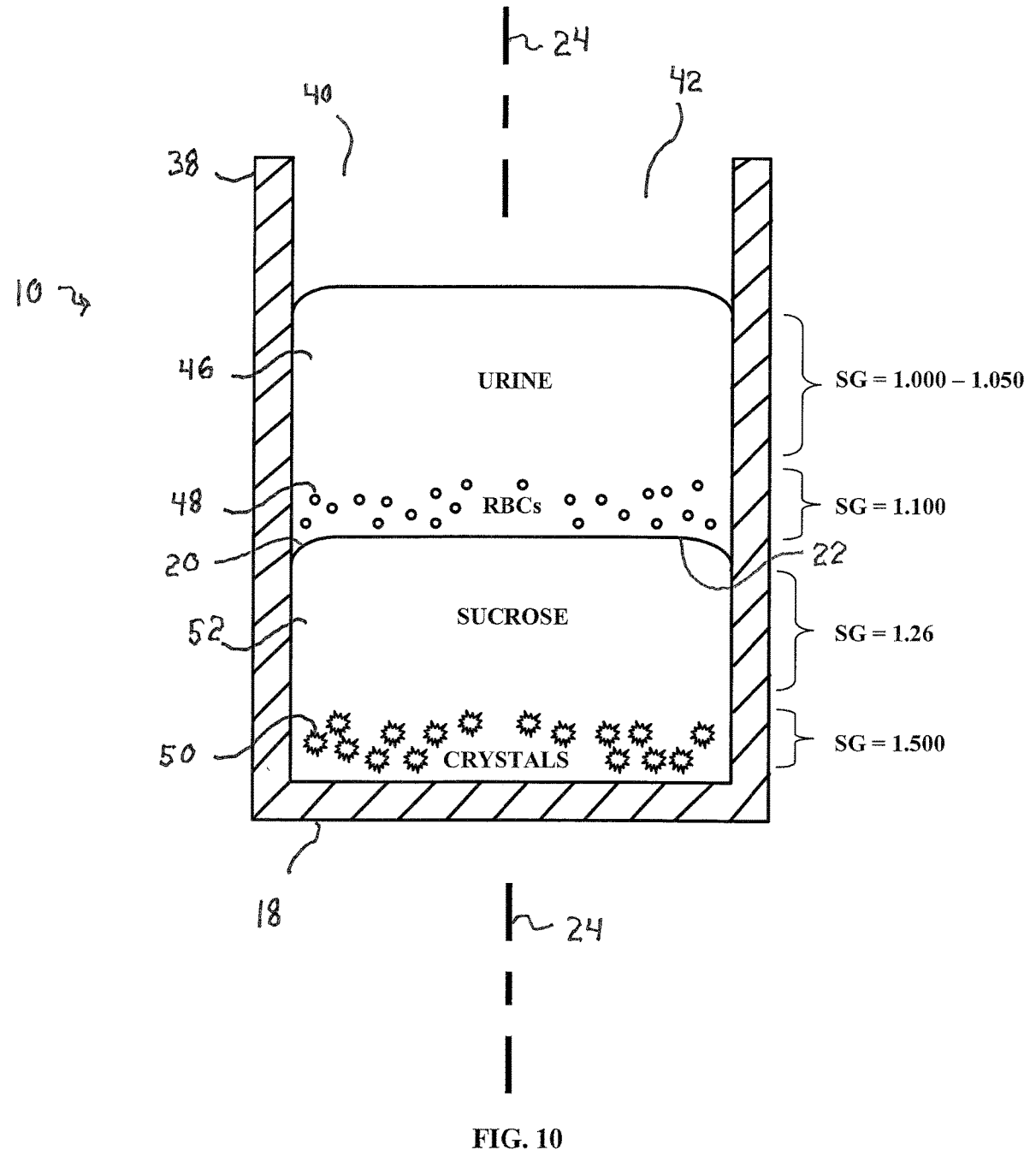
FIG. 10 is a simplified, longitudinal cross-sectional view of a collection container formed in accordance with the present disclosure and illustrating the separation and collection of particles of interest (red blood cells) at a fluidic imaging barrier formed between a urine specimen and a sucrose solution.

It is possible to orient optics in the standard or inverted configurations shown respectively in FIGS. 1A and 1B, or any other orientation in space, generally as long as the light emitted by the light source 8 provides sufficient illumination at a desired focal plane for the optical imaging system 2. In order to apply forces (e.g., centrifugal, gravitational and flotational) to the solid elements within the fluid structure, it may be necessary to orient the collection container 10 in a first disposition (e.g., in which the container's longitudinal axis 24 is disposed vertically, such as shown in FIG. 10), and that, after the solid elements have moved to a desired position within the container 10 and have reached equilibrium, where no appreciable further movement of the particles from this position is expected, the container 10 may be required to be oriented in a different, second disposition (e.g., in which the container's longitudinal axis 24 is disposed horizontally for imaging the collected particles through the side walls of the container 10). Once the container's orientation changes with respect to gravity, the fluids 12, 14, 16 will no longer be in equilibrium and everything within the container 10 (i.e., the fluids 12, 14, 16 and solid elements) will begin to seek a new state of equilibrium. This new equilibrium position likely will be contrary to the desired condition for the activities described above to concentrate the solid elements at a specific location within the container 10. For example, a collection container 10 could have forces applied by a swing arm centrifuge running in a vertical orientation so that the forces drive the solid elements to the top or bottom of the container 10 depending on the buoyant forces. The container 10 could then move to a microscopic scanning area in a horizontal position where the fluids 12, 14, 16 and solid elements are no longer in equilibrium and the restorative forces will require "significant" time to restore the particles to a new equilibrium position.

Judicious selection of container geometry as well as the properties of the fluids 12, 14, 16, such as viscosity, can maintain the solid elements in the desired physical location before moving to the new equilibrium location, thereby providing allowing the solid elements to be viewed. If the container 10 is designed to support imaging with a wide base and relatively short depth, then settling (or floating) of solid elements will be quickest and the imaging system 2 will have the best chance to see through the fluid, for example, when the container 10 is laid in a horizontal disposition for imaging through side walls. Furthermore, if the geometry (depth) of the interior dimensions of the container 10 is designed correctly, capillary action will provide a significant force supporting easy filling of the container 10. As will be described in greater detail, one such container (i.e., a Sedi-Vue™ cartridge) of the present disclosure is substantially closed to support alternate orientations or centrifugation to apply forces to the solid elements. The capillary forces can aid in filling the container 10 but can also be used to limit the speed at which the fluids and solid elements come to equilibrium when orientation is changed and gravity begins to pull in a different direction. In addition, choosing an appropriate viscosity for the immiscible fluids 12, 14, 16 will also impact the rate at which the solid elements reach a new equilibrium after an orientation change.

In some embodiments, the cartridge 24 is a SediVue™ cartridge manufactured by 77 Elektronika Muszeripari Kft. of Budapest, Hungary and sold by IDEXX Laboratories, Inc. of Westbrook, Maine and may be used in accordance with the present disclosure for holding a sample fluid 12 containing solid elements and one or more immiscible fluids 14, 16 having different specific gravities used in the formation of fluidic imaging barriers 22 at the interfaces 20 between the immiscible fluids. Such a container 24, without the fluids or fluidic imaging barriers formed therein, is disclosed in U.S. Pat. No. D681,843, titled Container For Analyzing Liquid and owned of record by 77 Elektronika Muszeripari Kft. of Budapest, Hungary, the disclosure of which is incorporated herein by reference, and is shown in FIG. 4 of the drawings. The fluid cartridge 24 shown in FIG. 4 has a fill port 30 communicating with an inlet chamber 28 moving up and to the left (when viewing FIG. 4) and opening into a fluid containing region 32, and also a vent port 34 for air to exhaust during filling. The structure of this particular container 10, modified in accordance with the present disclosure to include one or more fluidic imaging barriers 22 formed at the interfaces 20 between immiscible fluids 12, 14, 16 having different specific gravities, lends itself perfectly to meet the objectives of the present disclosure, and is used in experiments showing the efficacy of the modified container in separating and collecting solid elements carried by a sample fluid 12 at the fluidic imaging barriers 22, as will be described in greater detail.

Accordingly, integration of a container 10 with appropriate selection of fluids 12, 14, 16, and knowledge of the solid elements of interest for imaging with an optical system 2 and methods for applying forces to the container 10 and the fluids 12, 14, 16 and solid particles contained therein in desired directions can provide a viable solution for a test that desires to have a specified level of sensitivity defining the overall fluid volume based on the concentration of solid elements per volume, and limited time for sample processing and imaging. The container 10 and methodology of the present disclosure can be used for identifying many solid elements, but can be particularly valuable for biologic tests for solid elements in fluids, such as urine samples, fecal samples and other biological samples that will have relatively low amounts of solid elements that require their concentration for adequate detection and sensitivity.

FIGS. 5A-9B illustrate various forms of a container 10, such as a cuvette, test tube, centrifugation tube or cartridge, for holding a fluid 12 having particles 36 (also referred to herein as "solid elements") suspended therein and used for collecting the particles 36 in a particular volume and location within the container 10. The container 10 includes one or more barrier-forming fluids 14, 16 which cooperate with each other and/or with the fluid 12 in which particles of interest are suspended to form, as the case may be, one or more fluidic imaging barriers 22 at the interfaces 20 between the fluid 12 in which the particles 36 are suspended and the barrier-forming fluids 14, 16 adjacent to the fluid 12 having the suspended particles 36, or between adjacent barrier-forming fluids 14, 16. In one example, the fluid 12 having particles 36 suspended therein may be a whole blood sample, and the particles 36 of interest suspended therein to be collected and optically scanned by an optical imaging system 2 may include, but are not limited to, erythrocytes, leukocytes and thrombocytes. In another example, the fluid 12 having particles 36 suspended therein may be a urine sample, and the particles 36 of interest suspended therein to be collected may include, but are not limited to, crystals, cells and bacteria. In yet another example, the fluid 12 having particles suspended therein may be a flotation solution formed from an emulsified fecal sample, and the particles 36 of interest suspended therein may include, but are not limited to, parasite eggs and ova contained in the fecal sample, such as disclosed in the aforementioned U.S. patent application Ser. No. 17/363,279, titled "Collection Device and Method".

The fluid-holding container 10, shown by way of example in FIGS. 5A-9B as a collection tube, test tube or centrifugation tube, in one form is generally cylindrical having a closed bottom wall 18 and one or more side walls 38 extending from the bottom wall 18, which side wall or side walls 38 lead to and define a top opening 40 situated opposite the closed bottom wall 18 of the container 10. Thus, the bottom wall 18 and side wall or side walls 38 together define an interior cavity 42 of the container 10 for holding a fluid 12 to be tested and containing particles 36 to be collected for imaging. The fluid 12, such as the blood sample, urine sample or fecal flotation solution, is received by the interior cavity 42 of the container 10 through the top opening 40 thereof. Also, the barrier-forming fluid or fluids 14, 16 may be received by the interior cavity 42 through the top opening 40 of the container 10.

Figures 4A, 4B:
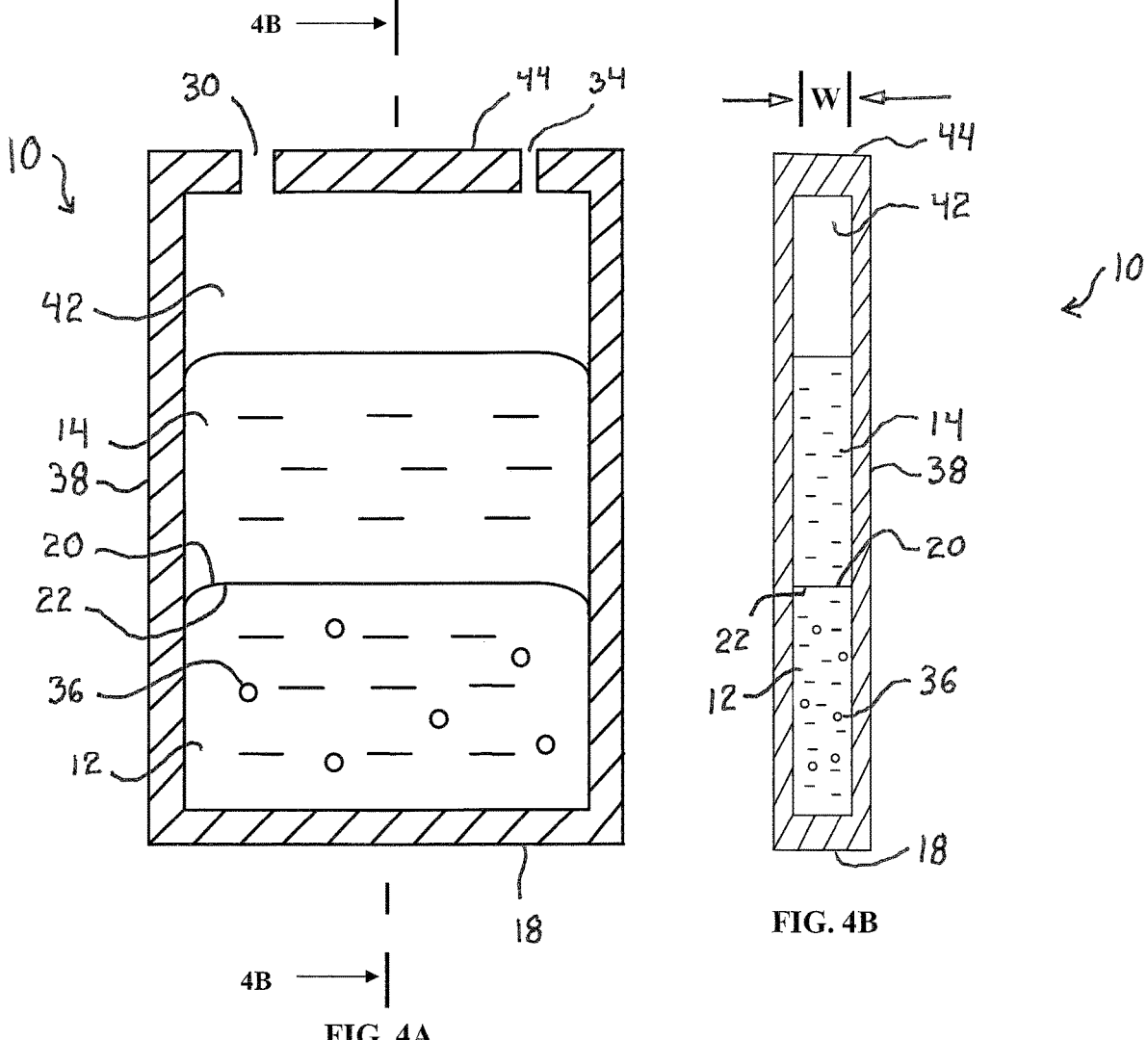
FIG. 4A is a cross-sectional view of a simplified form of a closed collection container formed in accordance with the present disclosure.
FIG. 4B is another cross-sectional view of the simplified form of the closed collection container shown in FIG. 4A, taken along line 4B-4B in FIG. 4A.

In another form, the container 10 may include a closed bottom wall 18, a closed top wall 44 and a side wall or side walls 38 extending between the closed top and bottom walls 44, 18 to define the interior cavity 42 of the container 10 as essentially a closed chamber except for a fluid inlet port 30 and a vent port 34, each of which is in communication with the interior cavity 42 of the container 10. A simplified form of such a container 10 is depicted in FIGS. 4A and 4B. An example of such a structured container 10 is the Sedivue™ cartridge mentioned previously and shown in FIG. 4 and FIGS. 11-14B of the drawings, which is sold by IDEXX Laboratories, Inc. of Westbrook, Maine.

As will be explained in greater detail in connection with the various embodiments of the collection container of the present disclosure shown by way of example in FIGS. 5A-9B and FIGS. 6 and 11-14B, each barrier-forming fluid 14, 16 forming part of the collection container 10 is chosen for having a particular specific gravity based on the specific gravity of the sample fluid 12 and the specific gravities of the particles 36 of interest suspended in the sample fluid 12, which particles 36 are to be separated and collected at the fluid imaging barriers 22 formed at the interface 20 between the sample fluid 12 and a barrier-forming fluid 14 adjacent to the sample fluid 12 and at the interface 20 between adjacent barrier-forming fluids 14, 16. Furthermore, each barrier-forming fluid 14, 16 is chosen to be immiscible with at least its adjacent barrier-forming fluid 14, 16. In another form of the collection container 10, the barrier-forming fluid 14 that is adjacent to the sample fluid 12 is selected to be immiscible with respect to the sample fluid 12. In yet another form of the collection container 10, each barrier-forming fluid 14, 16 is chosen to be immiscible with each other and with the sample fluid 12.

Figures 12A, 12B:
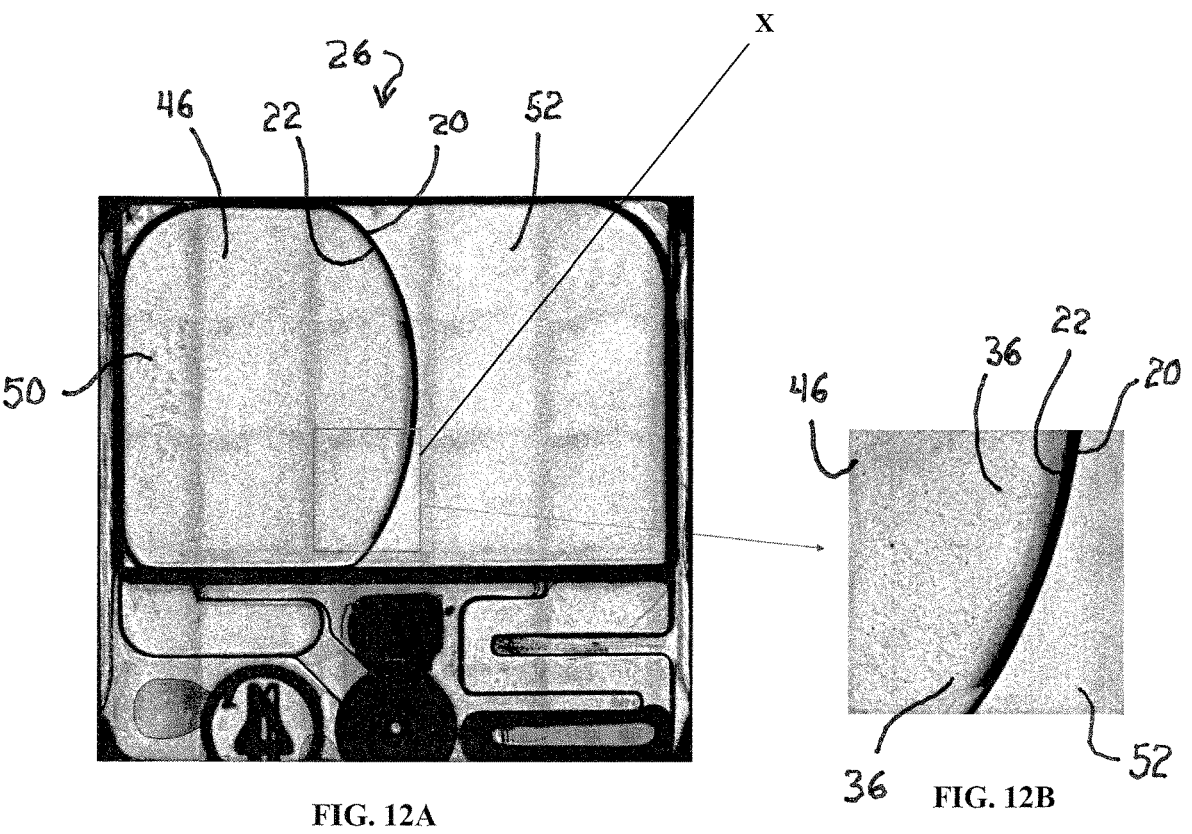
FIG. 12A is a photographic image of a container, such as that shown in FIGS. 4 and 11, used in a urine sediment analysis in which a first fluid held by the container is a urine sample and a second fluid held by the container is a sucrose solution, both the first and second fluids being immiscible with respect to one another and having different specific gravities and forming a fluidic imaging barrier at the interface between the first and second fluids.
FIG. 12B is an enlarged photographic image of a portion of the container shown in FIG. 12A and labeled with the letter "X" in FIG. 12A, and illustrating how cells separate from the urine sample and gravitate toward the fluidic imaging barrier at the interface between the urine sample (i.e., the first fluid) and the sucrose solution (i.e., the second fluid) and collect thereat.

Prior to describing in detail the various embodiments of the collection containers 10 of the present disclosure, reference should first be had to the example of the collection container 10 of the present disclosure shown in FIG. 10 as being used to separate solid elements 36 in a urine sample. Photographic images of a cartridge 24 embodied as a SediVue™ cartridge having formed therein a fluidic imaging barrier 22 and used in an actual experiment for separating red blood cells from a urine sample and collecting the red blood cells at the fluidic imaging barrier 22 are shown in FIGS. 12A and 12B and will be described in greater detail.

With reference to the simplified form of the collection container 10 shown in FIG. 10, a urine sample 46 generally has a specific gravity of about 1.000 to about 1.050. Red blood cells 48 in the urine sample 46 have a specific gravity of about 1.100, and crystals 50 in the urine sample 46 have a specific gravity of about 1.500. Thus, if the collection container 10 includes a barrier-forming fluid 14 having a specific gravity of about 1.200, such as a sucrose solution 52 of 1.26 in specific gravity, and the barrier-forming fluid (i.e., the sucrose solution 52) is immiscible with respect to a urine sample 46 added to the collection container 10, then in response to a passive force, such as gravity, or an active force, such as a centrifugal force, applied to the collection container 10 and imparted on the particles 36 of interest suspended in the urine sample 46 (in this example, red blood cells 48 and crystals 50), the red blood cells 48, having a specific gravity which is less than that of the barrier-forming sucrose solution 52, will separate from the urine sample 46 and collect at a fluidic imaging barrier 22 formed at the interface 20 between the sucrose solution 52 and the urine sample 46 but will not pass through the barrier 22 or the sucrose solution 52 having a greater specific gravity than that of the red blood cells 48. However, any crystals 50 suspended in the urine sample 46 will separate therefrom and pass through the barrier 22 and the sucrose solution 52, as the crystals 50 have a specific gravity which is greater than that of the barrier-forming sucrose solution 52, allowing the crystals 50 to pass therethrough. The above-described example of the collection container 10 of the present disclosure illustrated by FIG. 10 of the drawings advantageously may be used to separate red blood cells 48 from crystals 50 in a urine sample 46 and to collect the red blood cells 48 at the fluidic imaging barrier 22 formed at the interface 20 between the urine sample 46 and the adjacent barrier-forming sucrose solution 52.

The order in which the sample fluid 12, containing the particles 36 of interest, and the barrier-forming fluid or fluids 14, 16, are received by the collection container 10 varies in accordance with the requirements for separating and collecting the particles 36 of interest for later imaging. In one embodiment of the collection container 10, the sample fluid 12 is added first to the interior cavity 42 of the container 10 and occupies a predetermined volume of the interior cavity 42 located near the bottom 18 of the container 10. One or more barrier-forming fluids 14, 16 may be added atop the sample fluid 12 to occupy volumes of the container 10 located successively above the sample fluid 12 to form a fluidic imaging barrier 22 at the interface 20 between the sample fluid 12 and the next adjacent barrier-forming fluid

14, and to form fluidic imaging barriers 22 respectively at the interfaces 20 between mutually adjacent barrier-forming fluids 14, 16.

In yet another form of the collection container 10, the barrier-forming fluid or fluids 14, 16 may be added first to the interior cavity 42 of the container 10, and then the sample fluid 12 is added to the container 10. In this form of the collection container 10, the barrier-forming fluid 14, 16 having the greatest specific gravity is added first to the collection container 10, followed by barrier-forming fluids 14, 16 having successively lesser specific gravities before the sample fluid 12 is added to the collection container 10. In yet another form of the collection container 10 of the present disclosure, and when two or more immiscible barrier-forming fluids 14, 16 are used therein having different specific gravities, the fluids 14, 16 may be added to the collection container 10 in any order and not based on their relative specific gravities. The collection container 10 is then centrifuged for a sufficient period of time so that the barrier-forming fluids 14, 16 will rearrange within the interior cavity 42 of the collection container 10, with the barrier-forming fluid 14, 16 having the greatest specific gravity assuming a volume located within the interior cavity 42 of the collection container 10 nearest the bottom wall 18 of the container 10 and with each barrier-forming fluid 14, 16 having successively lesser specific gravities assuming locations above the bottom barrier-forming fluid 14, 16 in order of decreasing specific gravities. The sample fluid 12 containing the particles 36 of interest in suspension is then added to the collection container 10 atop the highest barrier-forming fluid 14, 16 having the least specific gravity of the barrier-forming fluids 14, 16.

In yet another form of the collection container 10 of the present disclosure, one or more barrier-forming fluids 14, 16 may be added to the interior cavity 42 of the container 10 to occupy lower locations in the container 10, the sample fluid 12 is then added to the interior cavity 42 of the collection container 10 to occupy a location therein on top of the previously-added barrier-forming fluid or fluids 14, 16, and then one or more additional barrier-forming fluids 14, 16 are added to the interior cavity 42 of the collection container 10 successively on top of the sample fluid 12.

The collection container 10, holding the fluid 12 having the particles 36 of interest in suspension, as well as having one or more barrier-forming fluids 14, 16 situated in the interior cavity 42 thereof, may be centrifuged for a sufficient period of time to impart a centrifugal force on the collection container 10 in a direction co-axial with the longitudinal axis 24 of the collection container 10, and impart a centrifugal force on the particles 36 suspended in the sample fluid 12 so as to cause the particles 36 to separate from the sample fluid 12 and collect at one or more of the fluidic imaging barriers 22 formed at the interface 20 between the sample fluid 12 and the barrier-forming fluid 14, 16 adjacent to the sample fluid 12, and at the interfaces 20 between adjacent barrier-forming fluids 14, 16 if more than one barrier-forming fluid 14, 16 is used in the collection container 10. Thus, centrifugation of the collection container 10 actively displaces the separated particles 36 toward a respective fluidic imaging barrier 22 where the particles 36 collect and may be scanned by an optical imaging system 2.

Alternatively, in a passive method, as opposed to the active method described above, flotational forces or gravitational forces may act on the container 10 and particles 36 suspended in the sample fluid 12 to cause the particles 36 to separate therefrom and respectively float or gravitate toward and collect at one or more fluidic imaging barriers 22 formed at the interface 20 between the sample fluid 12 and the barrier-forming fluid 14, 16 adjacent to the sample fluid 12 and at the interfaces 20 between adjacent barrier-forming fluids 14, 16 if more than one barrier-forming fluid 14, 16 is used in the collection container 10. The particles 36 collecting at the fluidic imaging barriers 22 may now be more readily imaged by an optical imaging system 2, requiring fewer scans to cover the smaller area in which the particles 36 collect.

Various forms of the collection container 10 of the present disclosure will now be described, and reference should be had to FIGS. 5A and 5B, 6A and 6B, 7A and 7B, 8A and 8B and 9A and 9B of the drawings. More specifically, FIGS. 5A-9B show a collection container 10 as described previously, having a closed bottom wall 18, one or more side walls 38 and a top opening 40, the walls 18, 38 defining an interior cavity 42 for receiving a sample fluid 12 having particles 36 suspended therein (see FIGS. 5A, 6A, 7A, 8A and 9A), and having one more barrier-forming fluids 14, 16 disposed within the interior cavity 42 of the collection container 10. The collection container 10 is used for holding a sample fluid 12 containing suspended particles 36, and for separating the particles 36 from the sample fluid 12 and collecting particles 36 of interest in a defined volume at or near where a fluidic imaging barrier 22 is formed. The particles 36 collecting at the fluidic imaging barrier 22 in a concentrated state may be more easily imaged, with fewer optical scans, by an optical imaging system 2. For imaging purposes, it is preferred if the side wall or walls 38 and/or the bottom wall 18 of the collection container 10 are made from a transparent or near-transparent material, such as glass, polyethylene, polycarbonate, polystyrene, cyclic olefin copolymer, or the like so that imaging of the collected particles 36 at the fluidic imaging barrier 22 can occur through the side walls 38 or bottom wall 18 of the collection container 10. It should be noted that the word "at" used herein and in the claims with reference to where the separated particles 36 collect relative to a fluidic barrier 22 is intended to have the inclusive meaning of the particles 36 being near or in proximity to the fluidic barrier 22.

Figures 5A, 5B:
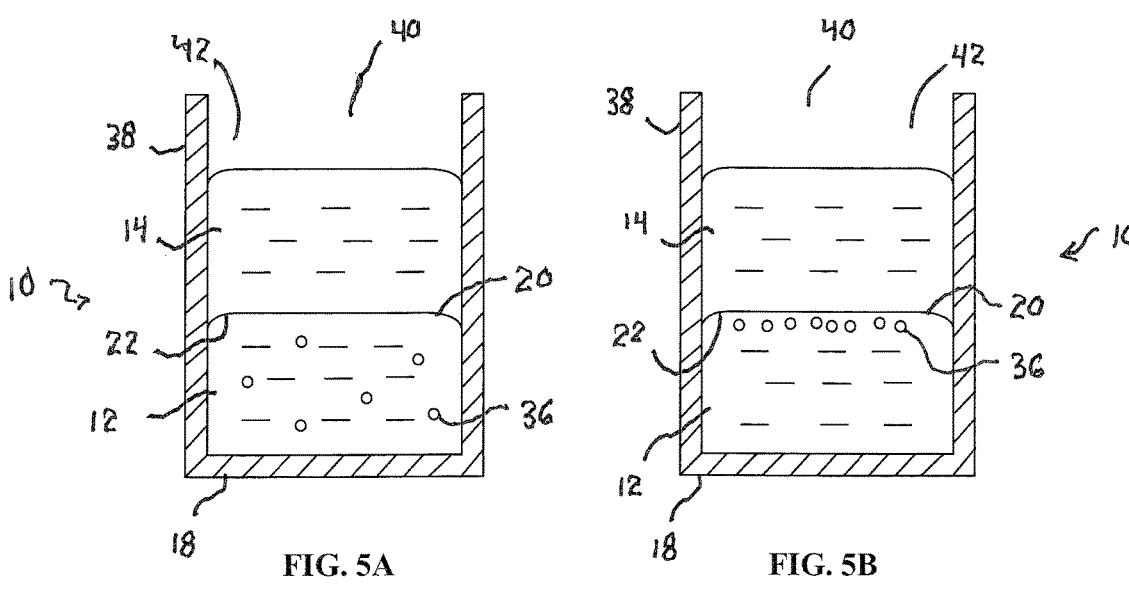
FIG. 5A is a simplified, longitudinal cross-sectional view of a collection container formed in accordance with the present disclosure.
FIG. 5B is a simplified, longitudinal cross-sectional view of the collection container of the present disclosure shown in FIG. 5A, and illustrating the collection of particles at a fluidic imaging barrier disposed within the collection container.

As shown in FIG. 5A, the collection container 10 includes the sample fluid 12 containing suspended particles 36, situated at a lower location within the interior cavity 42 of the collection container 10 near the bottom wall 18 thereof. The sample fluid 12 in this example is a liquid, and has a known or approximated specific gravity associated with it. Also, the particles 36 of interest suspended in the sample fluid 12 have specific gravities associated therewith, the specific gravities of the particles 36, in this example, being less than that of the sample fluid 12.

A barrier-forming fluid 14 is added to the interior cavity 42 of the collection container 10 and resides at a location above and in contact with the sample fluid 12. In this example of the collection container 10, the barrier-forming fluid 14 is also a liquid. The barrier-forming fluid 14 is chosen to be immiscible with the sample fluid 12 and to have a specific gravity which is less than the specific gravity of the sample fluid 12 and less than the specific gravities of the particles 36.

As shown in FIG. 5B, over a sufficient period of time, and as a result of flotational forces imparted on the particles 36, the "lighter" particles 36 relative to the sample fluid 12 will separate from their suspended state and float to the fluidic imaging barrier 22 formed at the interface 20 between the sample fluid 12 and the barrier-forming fluid 14 where the particles 36 will collect, in accordance with a passive flotation method of separating particles 36. The particles 36 cannot pass through the fluidic imaging barrier 22, since the specific gravity of the barrier-forming fluid 14 is less than the specific gravities of the particles 36. The particles 36 of the sample fluid 12, over time, will reach an equilibrium state and collect in a concentrated volume at the fluidic imaging barrier 22, where the concentration of particles 36 may be optically scanned by an optical imaging system 2 having, for example, the general structure shown in FIGS. 1A and 1B, through the bottom wall 18, top opening 40 or side walls 38 of the collection container 10.

It should be noted from FIG. 5A that the particles 36 float to the fluid imaging barrier 22 when the collection container 10 is in a vertical disposition, that is, when the longitudinal axis 24 of the collection container 10 (see FIG. 10) is co-axial and in alignment with a vertical axis. The particles 36 will remain in equilibrium and concentrated at the fluidic barrier 22 for imaging as long as the collection container 10 remains undisturbed and in an upright position. However, by also selecting a barrier-forming fluid 14 having a relatively high viscosity, and/or structuring the collection container 10 with a relatively small transverse width W (see FIG. 4B) between the interior surfaces of the side walls 38 such that capillarity and surface attraction between the container walls 38 and the fluids 12, 14 help maintain the fluids 12, 14 and particles 36 in their equilibrium state for a period of time, the collection container 10 may be subsequently oriented in a horizontal position, with its longitudinal axis 24 co-axial and in alignment with a horizontal axis, for imaging the concentration of particles 36 at the fluidic barrier 22 through its side walls 38 by the standard-configured and inverted-configured optical imaging systems 2 respectively shown in simplified form in FIGS. 1A and 1B. Because of the viscosity of the barrier-forming fluid 14 and/or the capillarity or surface attraction between the container walls 38 and the fluids 12, 14, the fluids 12, 14 and particles 36 collected at the fluid imaging barrier 22 will be slow to move from the vertical equilibrium state to a new horizontal equilibrium state, thereby providing the optical imaging system 2 sufficient time to optically scan the concentration of particles 36 at the fluidic imaging barrier 22.

Figures 6A, 6B:
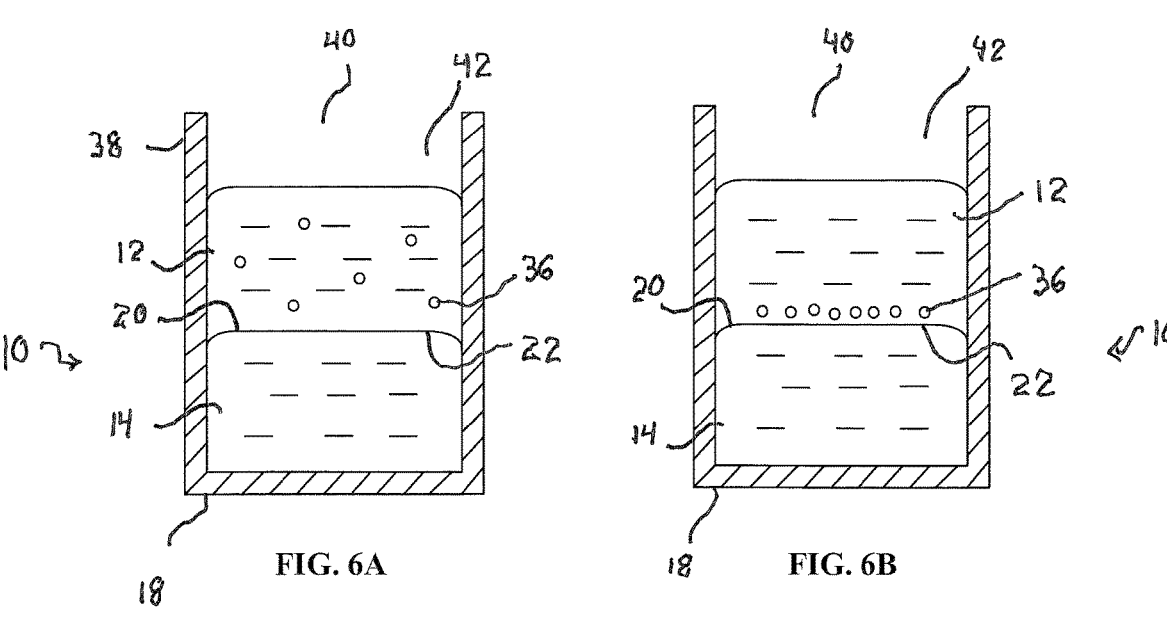
FIG. 6A is a simplified, longitudinal cross-sectional view of another collection container formed in accordance with the present disclosure.
FIG. 6B is a simplified, longitudinal cross-sectional view of the collection container of the present disclosure shown in FIG. 6A, and illustrating the collection of particles at a fluidic imaging barrier disposed within the collection container.

FIG. 6A is a cross-sectional view of another form of a collection container 10 of the present disclosure. The collection container 10 is similar in structure to that of the container 10 shown in FIG. 5A except that the container 10 has the barrier-forming fluid 14 situated at the lower portion of the interior cavity 42 of the collection container 10 that was occupied by the sample fluid 12 in the container 10 of FIG. 5A.

In the embodiment of the collection container 10 shown in FIG. 6A, the sample fluid 12 containing suspended particles 36 is added to the interior cavity 42 of the collection container 10 on top of the barrier-forming fluid 14. The specific gravity of the barrier-forming fluid 14 is greater than the known or approximated specific gravity of the sample fluid 12 and greater than the specific gravities of the particles 36 of interest suspended in the sample fluid 12. The specific gravities of the suspended particles 36 are greater than the specific gravity of the sample fluid 12. Furthermore, the barrier-forming fluid 14 is immiscible with respect to the sample fluid 12, and forms a fluidic imaging barrier 22 at the interface 20 between the sample fluid 12 and the barrier-forming fluid 14. In this example of the collection container 10, both the sample fluid 12 and the barrier-forming fluid 14 are liquids.

Thus, with this embodiment of the collection container 10, and as illustrated by FIG. 6B of the drawings, when a centrifugal force is applied to the collection container 10 in a direction along the longitudinal axis 24 of the container 10 and imparted on the particles 36 suspended in the sample fluid 12, in accordance with an active method for separating particles 36, or if a gravitational force is imparted on the container 10 and the suspended particles 36 of the sample fluid 12 when the container 10 is in an upright, vertical disposition, in accordance with a passive method of separating particles 36, the particles 36, being heavier than the sample fluid 12 in which they are suspended, will separate from the sample fluid 12 and be centrifugally forced or will gravitate toward the fluidic imaging barrier 22 situated at the interface 20 between the sample fluid 12 and the barrier-forming fluid 14. However, because the specific gravity of the barrier-forming fluid 14 is greater than the specific gravities of the separated particles 36, the particles 36 will not pass through the fluidic imaging barrier 22 and will collect at the barrier 22 in a concentrated volume thereat so that the concentration of particles 36 at the fluidic imaging barrier 22 may be imaged, with fewer optical scans, by an optical imaging system 2.

Figures 7A, 7B, 8A, 8B:
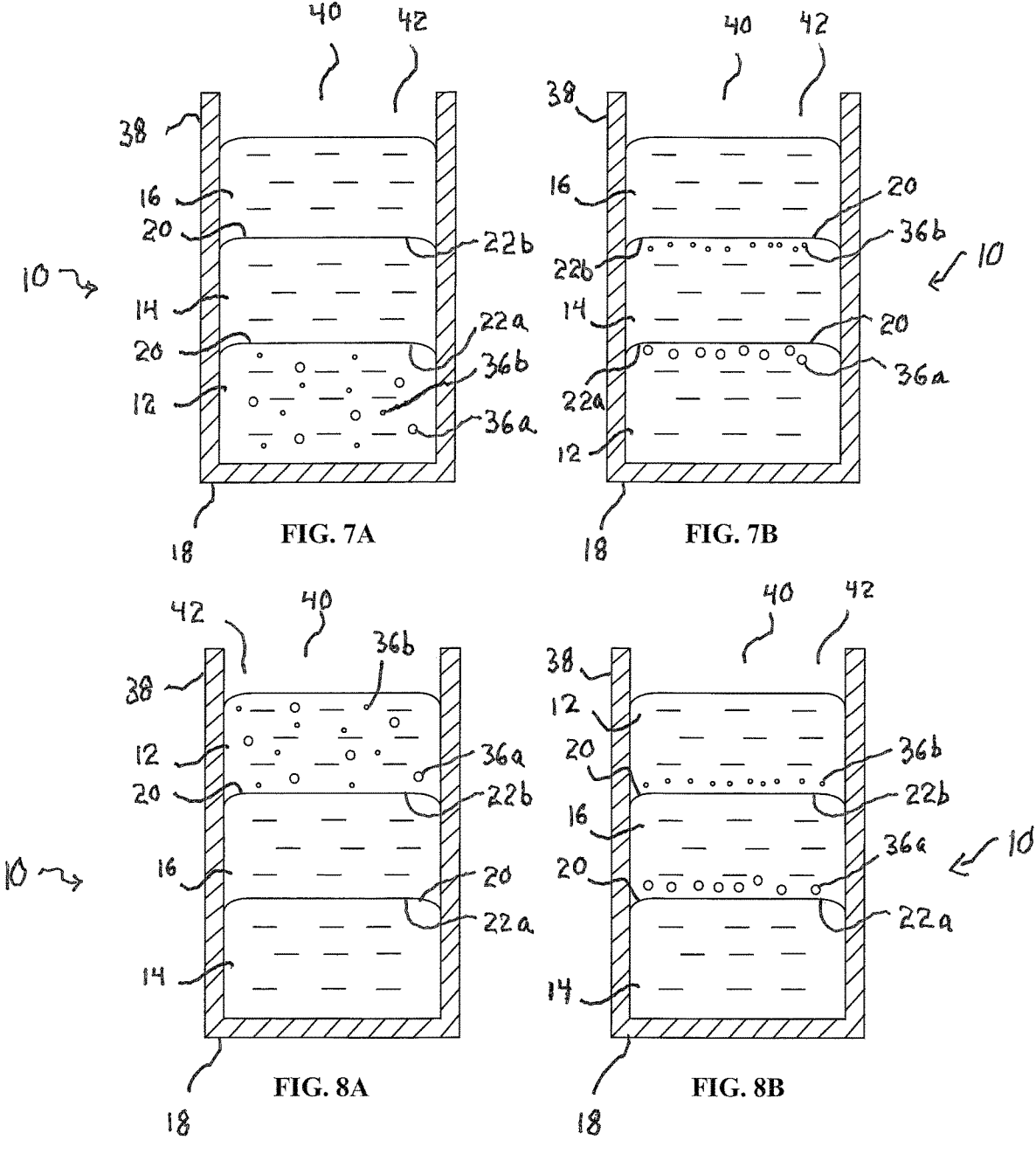
FIG. 7A is a simplified, longitudinal cross-sectional view of still another collection container formed in accordance with the present disclosure.
FIG. 7B is a simplified, longitudinal cross-sectional view of the collection container of the present disclosure shown in FIG. 7A, and illustrating the collection of particles at a fluidic imaging barrier disposed within the collection container.
FIG. 8A is a simplified, longitudinal cross-sectional view of yet another collection container formed in accordance with the present disclosure.
FIG. 8B is a simplified, longitudinal cross-sectional view of the collection container of the present disclosure shown in FIG. 8A, and illustrating the collection of particles at a fluidic imaging barrier disposed within the collection container.

FIG. 7A illustrates in cross-section yet another form of a collection container 10 of the present disclosure. The collection container 10 is similar in structure to those of the containers 10 shown in FIGS. 5A and 5B except that the container 10 has a plurality of barrier-forming fluids 14, 16 situated within the interior cavity 42 of the collection container 10 at an upper location and a middle location therein. The sample fluid 12 containing suspended particles 36a, 36b is added to the interior cavity 42 of the collection container 10 so that it resides in a volume of the container 10 at a lower location within the interior cavity 42 near the bottom wall 18 of the container 10. In the embodiment of the container 10 shown in FIG. 7A, two barrier-forming fluids 14, 16 are used although it is envisioned to form part of the present disclosure to have the container 10 include a plurality of barrier-forming fluids 14, 16.

A first barrier-forming fluid 14 is added to the interior cavity 42 of the collection container 10 so that it resides on top of and adjacent to the sample fluid 12 containing the particles 36a, 36b of interest. A second barrier-forming fluid 16 is added to the interior cavity 42 of the collection container 10 so that it resides on top of the first barrier-forming fluid 14 and adjacent to the first barrier-forming fluid 14. Each of the first and second barrier-forming fluids 14, 16 is immiscible with respect to one another, and at least the first barrier-forming fluid 14 or alternatively both of the first and second barrier-forming fluids 14, 16 are immiscible with respect to the sample fluid 12.

Furthermore, in the embodiment of the collection container 10 shown in FIG. 7A, the first barrier-forming fluid 14 has a specific gravity which is less than the known or approximated specific gravity of the sample fluid 12, and the second barrier-forming fluid 16 has a specific gravity associated therewith which is less than the specific gravity of the first barrier-forming fluid 14. Thus, the first barrier-forming fluid 14 defines with the sample fluid 12 a first fluidic imaging barrier 22a at the interface 20 between the first barrier-forming fluid 14 and the sample fluid 12. Additionally, the second barrier-forming fluid 16 forms a second fluidic imaging barrier 22b at the interface 20 between the second barrier-forming fluid 16 and the first barrier-forming fluid 14. In the example of the embodiment of the collection container 10 shown in FIG. 7A, each of the first barrier-forming fluid 14, the second barrier-forming fluid 16 and the sample fluid 12 is a liquid.

In the embodiment of the collection container 10 illustrated by FIG. 7A, the sample fluid 12 is shown with two types of particles 36a, 36b of interest, the first type of particles 36a being depicted in FIG. 7A as being larger than the second type of particles 36b. The first particles 36a, as shown as having the larger size in FIG. 7A, have specific gravities associated therewith which are less than the specific gravity of the sample fluid 12 and greater than at least the specific gravity of the first barrier-forming fluid 14. The second particles 36b of interest, shown in FIG. 7A as being smaller than the first particles 36a, have specific gravities associated therewith which are less than the specific gravity of the sample fluid 12 in which they are suspended, and are less than the specific gravity of the first barrier-forming fluid 14. However, the specific gravities of the second particles 36b are greater than the specific gravity of the upper, second barrier-forming fluid 16.

FIG. 7B illustrates the collection container 10 shown in FIG. 7A in an upright, vertical disposition and after a sufficient time has elapsed for the first and second particles 36a, 36b suspended in the sample fluid 12 to separate therefrom and collect at one of the first and second fluidic imaging barriers 22a, 22b in accordance with a passive flotation method. More specifically, in response to flotation forces imparted thereon, the first particles 36a, having specific gravities which are less than the specific gravity of the sample fluid 12 and greater than the specific gravity of the first barrier-forming fluid 14, will float upwardly in the interior cavity 42 of the collection container 10 and collect at the first fluidic imaging barrier 22a formed at the interface 20 between the sample fluid 12 and the first barrier-forming fluid 14. Because of their greater specific gravities relative to that of the first barrier-forming fluid 14, the first particles 36a will not pass through the first fluidic imaging barrier 22a and will concentrate thereat so that they may be more readily imaged, with fewer scans, by an optical imaging system 2.

The second particles 36b, shown in FIG. 7B as the smaller of the two types of particles 36a, 36b, also separate from the sample fluid 12 and float upwardly in the vertically disposed collection container 10, since the specific gravities of the second particles 36b are less than the specific gravity of the sample fluid 12. However, because the specific gravities of the second particles 36b are also less than the specific gravity of the first barrier-forming fluid 14, the second particles 36b will pass through the first fluidic imaging barrier 22a and float upwardly within the interior cavity 42 of the collection container 10 through the first barrier-forming fluid 14 until they reach the second fluidic imaging barrier 22b formed at the interface 20 between the first barrier-forming fluid 14 and the second barrier-forming fluid 16. The second particles 36b will collect in a concentrated volume at the second fluidic imaging barrier 22b and will not pass through the second fluidic imaging barrier 22b, as the specific gravities of the second particles 36b are greater than the specific gravity of the second barrier-forming fluid 16 residing at an upper location in the interior cavity 42 of the collection container 10.

As is evident from the forgoing description, the collection container 10 of the present disclosure shown in FIGS. 7A and 7B by way of example is advantageous in that it can separate multiple types of particles 36a, 36b of interest suspended in a sample fluid 12 at different fluidic imaging barriers 22a, 22b within the interior cavity 42 of the collection container 10 in concentrated volumes to facilitate the imaging of such separated particles 36a, 36b by an optical imaging system 2.

As with the embodiment of the collection container 10 shown in FIGS. 5A and 5B, the collection container 10 shown in FIGS. 7A and 7B may be placed in a horizontal disposition after the separated particles 36a, 36b collecting at the first and second fluidic imaging barriers 22a, 22b reach equilibrium and, thus, may be optically scanned by a standard or inverted optical imaging system 2 respectively depicted in a simplified form in FIGS. 1A and 1B. Just as with the collection container 10 shown in FIGS. 5A and 5B, the first and second barrier-forming fluids 14, 16 of the collection container 10 shown in FIGS. 7A and 7B may have a relatively high viscosity, and/or the collection container 10 is structured with a relatively small transverse width between the interior surfaces of the side walls 38, which provides additional capillarity and surface attraction between the container walls 38 and the fluids 12, 14, 16, each of which helps to maintain the fluids 12, 14, 16 and particles 36a, 36b in their equilibrium state for a period of time. Thus, the collection container 10 shown in FIGS. 7A and 7B, having a plurality of barrier-forming fluids 14, 16 and the formation therein of a plurality of fluidic imaging barriers 22a, 22b, may be subsequently oriented in a horizontal position, with its longitudinal axis 24 co-axial and in alignment with a horizontal axis, for imaging the particles 36a, 36b collecting at the fluidic barriers 22a, 22b through its side walls 38 by the standard-configured and inverted-configured optical imaging systems 2 respectively shown FIGS. 1A and 1B. The fluids 12, 14, 16 and particles 36a, 36b collected at the fluidic imaging barriers 22a, 22b will be slow to move from the vertical equilibrium state to a new horizontal equilibrium state, thereby providing the optical imaging system 2 with sufficient time to optically scan the concentration of particles 36a, 36b at their respective fluidic imaging barriers 22a, 22b.

Reference should now be had to FIG. 8A, which illustrates another form of a collection container 10 having a structure which is very similar to that of the collection container 10 shown in FIG. 7A. In the embodiment of the collection container 10 shown in FIG. 8A, a first barrier-forming fluid 14 is added to the interior cavity 42 of the collection container 10 and resides at a lower location therein near the bottom wall 18 of the collection container 10. A second barrier-forming fluid 16 is added to the collection container 10 to reside at a location above the first barrier-forming fluid 14, shown in FIG. 8A as occupying the middle portion of the interior cavity 42 of the collection container 10. A sample fluid 12 having particles 36a, 36b of interest suspended therein is added to the interior cavity 42 of the collection container 10 on top of the second barrier-forming fluid 16, and residing at a third location within the interior cavity 42 of the collection container 10, such as shown in FIG. 8A as occupying an upper portion of the interior cavity 42 of the collection container 10. As with the embodiment of the collection container 10 shown in FIGS. 7A and 7B, the sample fluid 12 added to the collection container 10 shown in FIG. 8A contains two types of particles 36a, 36b suspended therein which are desired to be separated from the sample fluid 12 and from each other and collected at different locations in the collection container 10 for optical imaging.

More specifically, the first barrier-forming fluid 14 in the embodiment of the collection container 10 shown in FIG. 8A, which occupies the lower portion of the collection container 10, has a specific gravity which is greater than the specific gravity of the second barrier-forming fluid 16, depicted in FIG. 8A as occupying a middle portion of the interior cavity 42 of the collection container 10. Similarly, the second barrier-forming fluid 16 has a specific gravity which is greater than the known or approximated specific gravity of the sample fluid 12. Furthermore, the first barrier-forming fluid 14 is immiscible with respect to the second barrier-forming fluid 16, and the first and second barrier-forming fluids 14, 16, or at least the second barrier-forming fluid 16, are immiscible with the sample fluid 12 containing the suspended particles 36a, 36b. Thus, the first barrier-forming fluid 14 forms a first fluidic imaging barrier 22a at the interface 20 between the first barrier-forming fluid 14 and the second barrier-forming fluid 16. Similarly, the second barrier-forming fluid 16 forms a second fluidic imaging barrier 22b at the interface 20 between the second barrier-forming fluid 16 and the sample fluid 12. In the embodiment of the collection container 10 shown in FIG. 8A, each of the sample fluid 12, the first barrier-forming fluid 14 and the second barrier-forming fluid 16 is a liquid. Although only two barrier-forming fluids 14, 16 are shown as being used in the collection container 10 depicted in FIG. 8A, it should be understood that a plurality of barrier-forming fluids 14, 16 may be added to the collection container 10 to form a plurality of fluid imaging barriers 22a, 22b so that different types of particles 36a, 36b of interest may be separated from a sample fluid 12 and collect in a concentrated volume at different fluid imaging barriers 22a, 22b for imaging by an optical imaging system 2.

As with the embodiment of the collection container 10 shown in FIGS. 7A and 7B, the collection container 10 of FIG. 8A is capable of separating different types of particles 36a, 36b suspended in the sample fluid 12. Rather than using the passive flotation method for separating these particles, as described in connection with the collection container 10 shown in FIGS. 7A and 7B, the collection container 10 shown in FIG. 8A may be centrifuged to separate different types of particles 36a, 36b from the sample fluid 12 and to collect the different types of particles 36a, 36b at respective fluidic imaging barriers 22a, 22b within the collection container 10 in accordance with an active separation method. Alternatively, the collection container 10 may be left in an upright, vertical disposition for a sufficient period of time to allow gravity to act on the particles 36a, 36b such that the particles 36a, 36b separate from the sample fluid 12 and collect at different respective fluidic imaging barriers 22a, 22b in accordance with a passive method for separating the particles 36a, 36b.

More specifically, depicted in FIG. 8A within the sample fluid 12 are two different types of particles 36a, 36b, the first particles 36a being shown as having a larger size than that of the second particles 36b. The first particles 36a have specific gravities which are greater than the specific gravity of the sample fluid 12 in which they are suspended. Furthermore, the first particles 36a, depicted in FIG. 8A as being the larger of the particles 36a, 36b, have specific gravities which are greater than the specific gravity of the second barrier-forming fluid 16, but have specific gravities which are less than the specific gravity of the first barrier-forming fluid 14.

The second type of particles 36b, which particles 36b are depicted in FIG. 8A as being smaller than the first particles 36a, have specific gravities which are greater than the specific gravity of the sample fluid 12 in which they are suspended, but the specific gravities of the second particles 36b are less than the specific gravities of the second barrier-forming fluid 16 and the first barrier-forming fluid 14.

Accordingly, and as shown in FIG. 8B of the drawings, when the collection container 10 is subjected to either centrifugal forces or gravitational forces for a sufficient period of time, the first and second particles 36a, 36b will separate from the sample fluid 12 in which they were suspended and will be centrifugally forced, or will gravitate, toward one of the first fluidic imaging barrier 22*a* and the second fluidic imaging barrier 22*b*. As depicted in FIG. 8B, the heavier first particles 36*a*, having specific gravities which are greater than the specific gravities of the sample fluid 12 and the second barrier-forming fluid 16 but less than the specific gravity of the first barrier-forming fluid 14, will separate from the sample fluid 12 in which they were suspended and will be centrifugally forced or will gravitate downwardly through the interior cavity 42 of the collection container 10 through the upper, second fluidic imaging barrier 22*b*, and will collect at the lower, first fluidic imaging barrier 22*a*. The first particles 36*a* will not pass through the first fluidic imaging barrier 22*a*, as their specific gravities are less than the specific gravity of the first barrier-forming fluid 14. The first particles 36*a* will collect at the lower, first fluidic imaging barrier 22*a* in a concentrated volume where they may be imaged, with fewer scans, by an optical imaging system 2.

As also depicted in FIG. 8B, the lighter second particles 36*b* suspended in the sample fluid 12 will separate from the sample fluid 12 and will be forced or will gravitate toward the second fluidic imaging barrier 22*b* under the influence of centrifugal or gravitational forces, respectively, as the specific gravities of the second particles 36*b* are greater than the specific gravity of the sample fluid 12 in which they were suspended. The second particles 36*b* will not pass through the upper, second fluidic imaging barrier 22*b*, as their specific gravities are less than the specific gravity of the second barrier-forming fluid 16. Accordingly, the second particles 36*b* will collect at the second fluidic imaging barrier 22*b* in a concentrated volume thereat so that they may be more readily imaged, with fewer scans, by an optical imaging system 2.

Figures 9A, 9B:
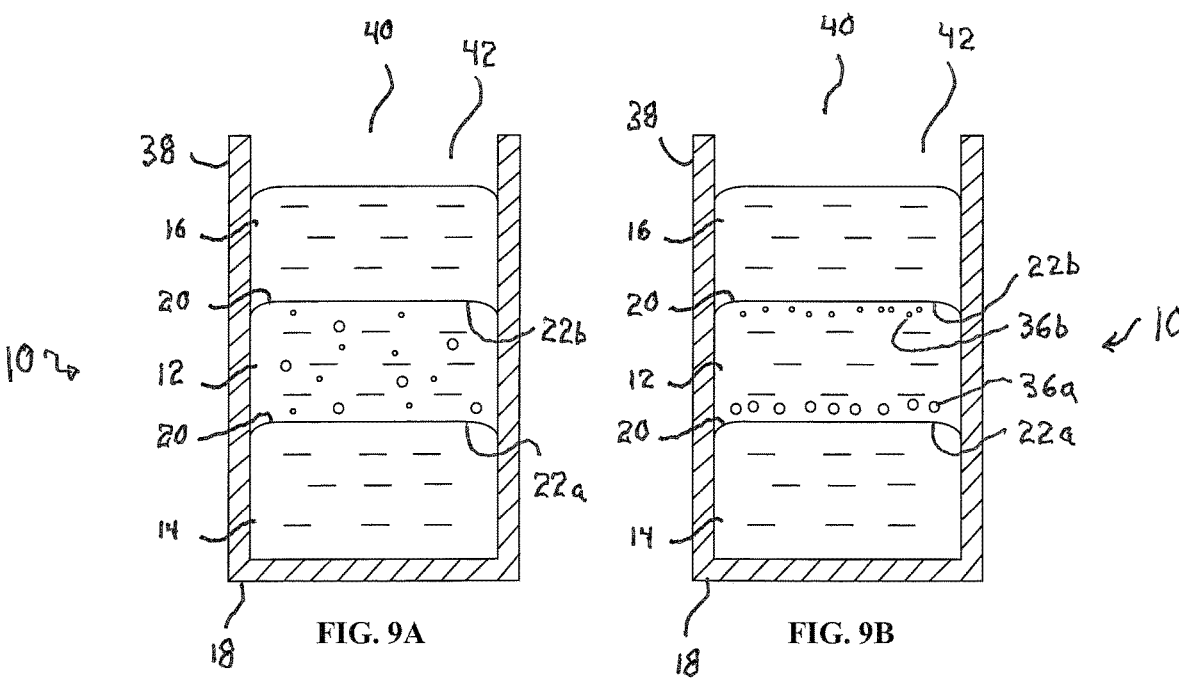
FIG. 9A is a simplified, longitudinal cross-sectional view of still another collection container formed in accordance with the present disclosure.
FIG. 9B is a simplified, longitudinal cross-sectional view of the collection container of the present disclosure shown in FIG. 9A, and illustrating the collection of particles at a fluidic imaging barrier disposed within the collection container.

FIG. 9A illustrates yet another embodiment of a collection container 10 having two or more barrier-forming fluids 14, 16 similar to the embodiment of the collection container 10 shown in FIGS. 8A and 8B. In the embodiment of the collection container 10 shown in FIG. 9A, the sample fluid 12 having particles 36*a*, 36*b* of interest suspended therein is interposed between a lower, first barrier-forming fluid 14 and an upper, second barrier-forming fluid 16. More specifically, the first barrier-forming fluid 14 occupies a first location within the interior cavity 42 of the collection container 10 situated near the bottom wall 18 of the container 10 at the lower portion of the interior cavity 42. Then, a sample fluid 12 having particles 36*a*, 36*b* suspended therein which are to be separated from the sample fluid 12 is added to the interior cavity 42 of the collection container 10 on top of the first barrier-forming fluid 14 and occupying a second location within the interior cavity 42 of the collection container 10, which is depicted in FIG. 9A as being at the middle portion of the interior cavity 42. After the sample fluid 12 is added to the collection container 10, a second barrier-forming fluid 16 is added to the interior cavity 42 of the collection container 10 atop the particle-containing sample fluid 12 so that it occupies a third location within the interior cavity 42 of the collection container 10, which is depicted in FIG. 9A as being at the upper portion of the interior cavity 42 of the container 10.

In the embodiment of the collection container 10 shown in FIG. 9A, the first barrier-forming fluid 14 is chosen to have a specific gravity which is greater than the known or approximated specific gravity of the sample fluid 12. The second barrier-forming fluid 16 is chosen to have a specific gravity which is less than the specific gravity of the sample fluid 12. The first and second barrier-forming fluids 14, 16 are immiscible with respect to at least the sample fluid 12 but may also be immiscible with respect to one another so that a first fluidic imaging barrier 22*a* is formed at the interface 20 between the first barrier-forming fluid 14, residing in the lower portion of the interior cavity 42 of the container 10, and the sample fluid 12, and a second fluidic imaging barrier 22*b* is formed at the interface 20 between the sample fluid 12 and the second barrier-forming fluid 16, residing at the upper portion of the interior cavity 42 of the collection container 10. In the example of the embodiment of the collection container 10 shown in FIG. 9A, each of the first barrier-forming fluid 14, the second barrier-forming fluid 16 and the sample fluid 12 is a liquid.

As in the embodiment of the collection container 10 illustrated by FIGS. 8A and 8B, the collection container 10 of FIG. 9A may be used to separate different types of particles 36*a*, 36*b* of interest that are suspended in the sample fluid 12, preferably in response to flotational forces and gravitational forces imparted on the container 10 and the particles 36*a*, 36*b* suspended in the sample fluid 12 while the container 10 is in an upright, vertical disposition and in accordance with a passive method of separating particles. More specifically, the sample fluid 12 has suspended therein different types of particles 36*a*, 36*b* which are desired to be separated for imaging. Even more specifically, a first type of particles 36*a* is depicted in FIG. 9A as being of a larger size, and a second type of particles 36*b* is depicted in FIG. 9A as having a smaller size relative to the first type of particles 36*a*. The first particles 36*a* have specific gravities which are greater than the specific gravity of the sample fluid 12 in which they are suspended, and the specific gravities of the first particles 36*a* are less than the specific gravity of the first barrier-forming fluid 14 occupying the lower portion of the interior cavity 42 of the collection container 10. The second particles 36*b*, depicted in FIG. 9A as being smaller than the first particles 36*a*, have specific gravities which are less than the specific gravity of the sample fluid 12 in which they are suspended, and have specific gravities which are greater than the specific gravity of the second barrier-forming fluid 16 residing at the upper portion of the interior cavity 42 of the collection container 10.

The collection container 10 of this embodiment of the present disclosure is shown to be in an upright, vertical disposition in FIGS. 9A and 9B. When in a vertical disposition, and as shown in FIG. 9B, under the influence of gravitational and flotational forces imparted on the first and second particles 36*a*, 36*b* suspended in the sample fluid 12, the first and second particles 36*a*, 36*b* will separate from the sample fluid 12. The heavier first particles 36*a* will gravitate downwardly in the collection container 10 toward the first fluidic imaging barrier 22*a* where they will collect. The first particles 36*a* will not pass through the first fluidic imaging barrier 22*a*, as the specific gravities of the first particles 36*a* are less than the specific gravity of the first barrier-forming fluid 14 occupying the lower portion of the interior cavity 42 of the collection container 10. The first particles 36*a* will collect at the first fluidic imaging barrier 22*a* in a concentrated volume thereat where they may be more readily imaged, with fewer scans, by an optical imaging system 2.

The lighter second particles 36*b* suspended in the sample fluid 12 will separate from the sample fluid 12 and float upwardly in the interior cavity 42 of the collection container 10 toward the second fluidic imaging barrier 22*b*. The second particles 36*b* will not pass through the second fluidic imaging barrier 22*b*, as the specific gravities of the second particles 36*b* are greater than the specific gravity of the second barrier-forming fluid 16 occupying the upper portion of the interior cavity 42 of the collection container 10. The second particles 36b will collect at the second fluidic imaging barrier 22b in a concentrated volume, where the second particles 36b may be more readily imaged, with fewer scans, by an optical imaging system 2.

Although only two barrier-forming fluids 14, 16 are shown in FIGS. 9A and 9B as being added to the interior cavity 42 of the collection container 10, it is envisioned to be within the scope of the present disclosure to provide a collection container 10 having a plurality of barrier-forming fluids 14, 16 within the interior cavity 42 of the collection container 10 and thus forming a plurality of fluidic imaging barriers 22a, 22b within the interior cavity 42 for separating different particles 36a, 36b of interest having different specific gravities that are suspended in a sample fluid 12.

Figure 11:
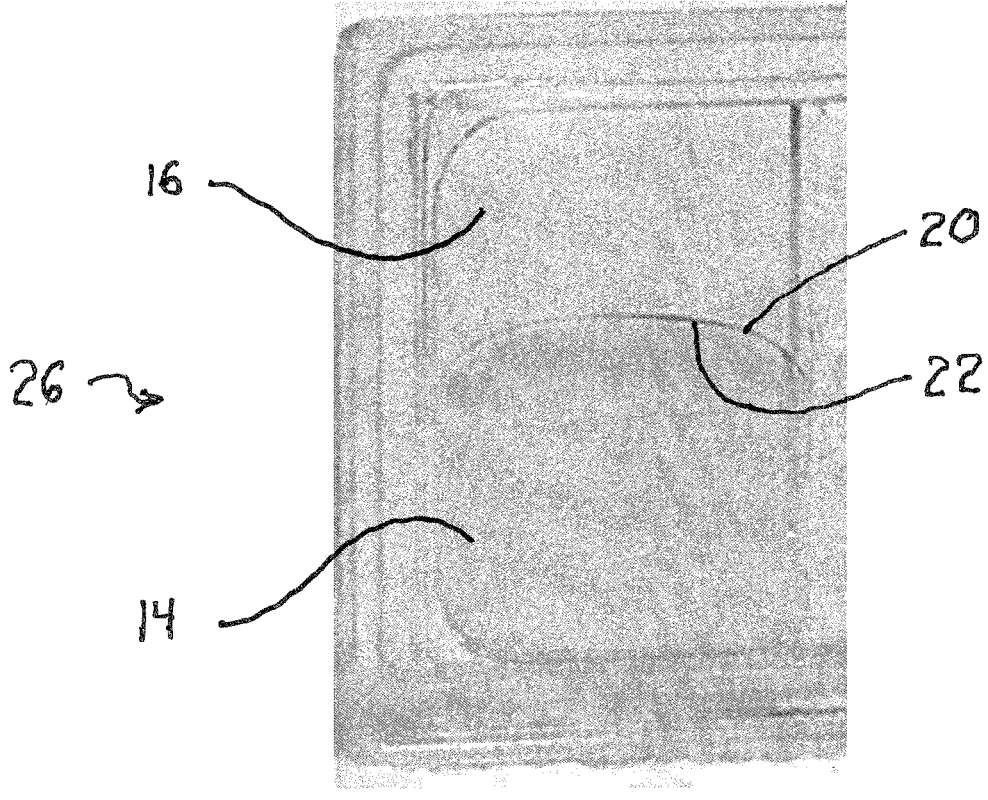
FIG. 11 is a photograph of a portion of the container shown in FIG. 4 modified to include two immiscible fluids having different specific gravities and showing the equilibrium separation of the two fluids and the formation of a fluid imaging barrier at the interface of the two fluids.

An example of the present disclosure using zinc sulfate (ZnSO$_4$) as one fluid 14 and oleyl alcohol as another fluid 16 shows that the two fluids 14, 16, which are immiscible with respect to each other and which have different specific gravities, will clearly separate in an enclosed container 10 that is approximately 2.5 centimeters×2.5 centimeters×0.1 centimeters in outer dimensions, causing a fluidic imaging barrier 22 to be formed at the meniscus interface 20 between the two fluids 14, 16. The different specific gravities of the two fluids 14, 16 provide the desired effect of creating a small contained zone at the interface 20 of the two fluids 14, 16 for any solid elements 36 that have specific gravities between those of the two fluids 14, 16. FIG. 11 is a photograph of a portion of a cartridge 26 embodied as a SediVue™ cartridge shown in FIG. 4 containing the two fluids 14, 16 mentioned above, and shows the clear separation and line of demarcation at the fluidic imaging barrier 22 formed at the interface 20 between the fluids 14, 16. Zinc sulfate fluid 14 has a specific gravity of about 1.180 and is shown in the photograph of FIG. 11 as being the fluid 14 residing in the lower portion of the cartridge 26, when viewing FIG. 11. Oleyl alcohol has a specific gravity of between about 0.845 and about 0.855 and is shown in the photograph of FIG. 11 as being the fluid 16 residing in the upper portion of the cartridge 26, when viewing FIG. 11. Optical scans by an optical imaging system 2 would be directed to the volume of the cartridge 26 in proximity to the fluidic imaging barrier 22 formed at the interface 20 between the two immiscible fluids 14, 16 where separated particles 36 of interest will collect.

Practical Examples

Two relevant examples in which a collection container 10 having one or more fluidic imaging barriers 22 constructed in accordance with the present disclosure may be advantageously used include ova and egg float methodologies used in the detection of intestinal parasites excreted in fecal samples, and urine sedimentation methodologies used for identifying formed elements in urine samples. Both of these techniques are commonly performed manually and use wet samples on a slide under a microscope. Each technique is described below.

Urine sediment analysis is commonly performed in conjunction with a physical examination and urine chemistry test as part of a full workup to determine patient health status. The standard manual approach is to extract a urine sample, place it in a cuvette and then place the cuvette in a centrifuge. The centrifugation process is gentle, but the purpose is to force all of the formed elements (red cells, white cells, crystals, epithelial cells, casts, bacteria, etc.) to the bottom of the cuvette. The supernatant is then mostly removed, generally by pour off or using a pipette, leaving the concentrated sediment and a small amount of fluid. The sample is then dispensed onto a microscope slide with a coverslip or microtiter plate well and evaluated using a microscope at 100× magnification and 400× magnification. The technician then identifies the formed elements present and reports his observations, generally in a semi-quantitative manner.

Automated urine sediment analysis attempts to produce similar results, generally with a similar approach. The IDEXX SediVue Dx™ analyzer accepts neat (not centrifuged) urine into a cartridge. The cartridge is then sent through a vertical centrifuge with a primary function to apply force to the formed elements and encourage them to quickly move to the bottom of the cartridge. Once the formed elements are at the bottom of the cartridge, the automated digital microscope of the SediVue Dx™ instrument analyzes the bottom layer of the cartridge, identifies the formed elements, and generates a report of what is found, with associated digital microscope images.

Using the aforementioned SediVue Dx™ analyzer, the formed elements will be forced to the bottom of the cartridge, but randomly across the whole cartridge. The resulting impact is that a large number of fields of view must be analyzed in order to get a reasonable statistical representation of what is in the sample. In this case, 70 locations are captured, representing about 10 microliters (ul) of neat sample. The entire process is complete in about three minutes. The cartridge contains about 165 microliters (ul) of sample, and about 10 microliters (ul) are optically scanned. If there was a desire to interrogate more of the sample, or to concentrate the 165 microliters (ul) into a smaller region of the cartridge, then the collection container 10 of the present disclosure could be advantageously used. For example, the SediVue™ cartridge 26 shown in FIG. 11 having two immiscible fluids 14, 16 with different specific gravities and forming a fluidic imaging barrier 22 at the interface 20 between the two fluids 14, 16 may be used.

Figure 2:
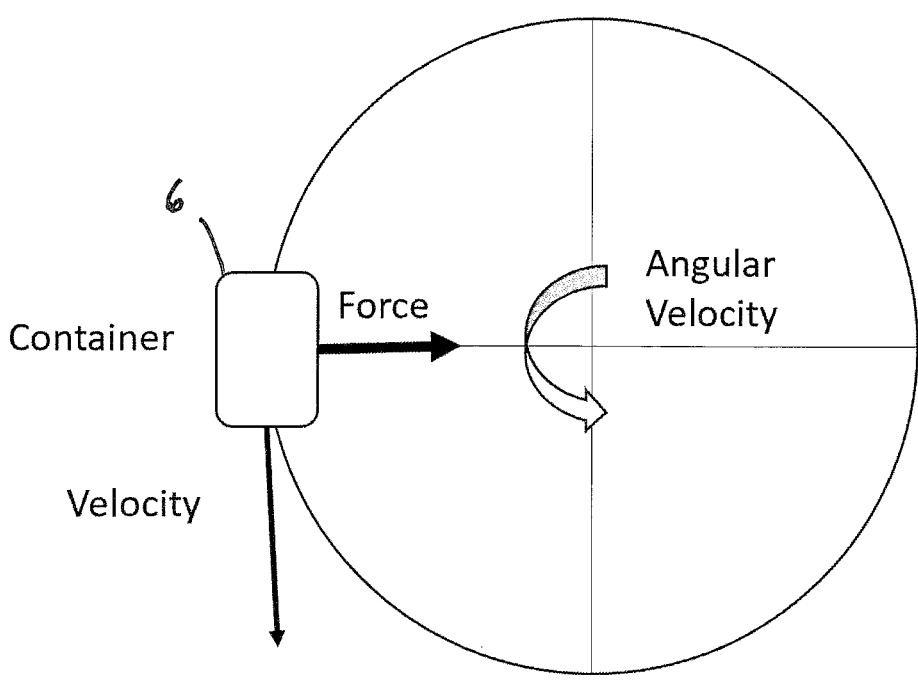
FIG. 2 is a diagrammatic view of forces applied by centrifugation to a container to move solid elements suspended in a fluid held by the container laterally with respect to an imaging interface and concentrating the solid elements into a smaller physical imaging area.

The vertical centrifuge spinning in a single direction will exert forces on the cartridge from the center point, such as illustrated by FIG. 2 of the drawings, and the formed elements would be forced to the bottom of the cartridge. If alternate sequences were performed with the vertical centrifuge, it is possible to apply forces that drive the formed elements to one side of the cartridge or the other. One possible method would be to hold the vertical centrifuge so the cartridge is at the 3:00 clock face location and allow gravity to pull the formed elements to the side of the cartridge (it is the bottom from a gravity perspective in this orientation). To speed up the effects of gravity, acceleration profiles with rapid braking could also force the formed elements to one side of the cartridge.

As explained earlier, the problem with this approach is that the edge or walls of the cartridge have some undesired features for imaging, such as welding debris related to the manufacturing of the molded cartridge, imperfections and other artifacts. Such artifacts and the like may affect the accuracy of optical scanning of particles 36 accumulating at the bottom wall or side walls of the cartridge. An algorithm in the processor of the optical imaging system 2 is required to account for such artifacts. Accordingly, it would be preferred to collect the particles 36 for imaging at a location in the cartridge away from the bottom wall and side walls of the cartridge. Thus, and in accordance with the present disclosure, by adding an additional immiscible fluid 14 to the sample fluid 12 in the cartridge 26 with a greater specific gravity than those of the formed elements 36 and the sample fluid 12 in which the formed elements 36 are suspended, a fluidic imaging barrier 22 may be formed at the interface 20 between the sample fluid 12, such as in this example a urine sample 46, and the additional immiscible fluid 14 having a relatively greater specific gravity. The fluidic imaging barrier 22 thus formed at the interface 20 between the urine sample 46 and the immiscible fluid 14 having a greater specific gravity will provide a location away from the cartridge bottom wall 18 and side walls 38 where the formed elements 36 can collect and be imaged.

For the case of urine sediment, and as described previously with reference to FIG. 10 of the drawings, some of the formed elements 36 will be very dense, such as crystals 50 for example, and they can be separated from lower density formed elements, such as cells 48 and bacteria. As mentioned previously, urine 46 is basically water with a bit of salt in it and generally has a specific gravity of between about 1.000 and about 1.050. Red blood cells (RBCs) 48 will generally have a specific gravity near 1.100, and crystals 50 will generally have a specific gravity greater than about 1.500. If a barrier-forming fluid 14 is selected with a specific gravity near 1.200, then the cells 48 will be trapped between the sample fluid 12 (in this example, urine 46) and the barrier-forming fluid 14 at the interface 20 between the two fluids 12, 14 where the fluidic imaging barrier 22 is formed, but the crystals 50 will continue to move to the bottom wall 18 or side walls 38 of the cartridge 26/container 10 in response to gravitational or centrifugal forces applied to the cartridge 26/container 10 and imparted on the solid elements 36 suspended in the urine sample 46. Thus, the method of separating and collecting particles 36 at one or more fluidic imaging barriers 22 in a collection container 10 in accordance with the present disclosure is advantageous over known methods of separating particles 36, and in the case of urine sedimentation as described above, can be used for separating crystalline debris 50 from cells 48 of interest, not only concentrating the cells 48 at a location in the collection container 10 away from the bottom wall 18 and side walls 38 of the container 10, but also making the cells 48 easier to separate from non-cells.

FIGS. 12A and 12B show microscopic images at 400× magnification of cells 48 in a urine sample 46 moving towards and concentrating at the fluidic imaging barrier 22 formed at the interface 20 of the urine sample 46 and a sucrose solution 52 having a specific gravity of about 1.26 in a SediVue™ cartridge 26. The cartridge 26 was centrifuged while in a vertical disposition, and then placed on its side in a horizontal disposition for imaging the particles 36 which have separated from the urine sample 46 using an optical imaging system 2 such as shown in FIG. 1A or FIG. 1B. FIG. 12B is an enlarged view of a portion of the image of the Sedivue™ cartridge 26 shown in FIG. 12A, and shows that the cells 48 of interest do not move past the fluidic imaging barrier 22 formed at the interface 20 between the two fluids 12, 14. Furthermore, and as can be seen in the image of the cartridge 26 shown in FIG. 12A, the heavier crystals 50 separated from the urine sample 46 congregated near the bottom wall 18 of the cartridge 26 (see the left side of the cartridge 26 when viewing FIG. 12A).

In a conventional flotation method for separating ova and eggs from a fecal sample to determine if the patient is afflicted with parasites, as described in more detail in aforementioned U.S. patent application Ser. No. 17/363,279, titled "Collection Device and Method", the conventional manual testing methodology includes the steps of collecting a fecal sample, mechanically separating the sample (by vigorously shaking the container, for example) to release the ova and eggs into a flotation solution (commonly zinc sulfate, $ZnSO_4$), and either using centrifugation to allow the ova and eggs to float to the top surface of the solution or waiting passively for gravity to float the ova and eggs to the top surface of the solution. Once the ova and eggs have floated to the surface (and there is a positive meniscus above the open top of the container), a microscope coverslip is placed on the top of the container in contact with the solution's meniscus to capture the floating ova and eggs by surface tension. Then, the coverslip is placed on a microscope slide and analyzed manually using a microscope typically under 100× and 400× magnification. Ova and eggs are then identified by a technician and reported. Such a conventional method is time consuming and inefficient.

However, using the method of the present disclosure and a collection container 10 having one or more immiscible, barrier-forming fluids 14, 16 with pre-selected specific gravities to define fluidic imaging barriers 22 at the interfaces 20 between the barrier-forming fluids 14, 16 and a sample fluid 12 or between adjacent barrier-forming fluids 14, 16 in an automated fecal flotation separation method, results similar to those described previously for the urine sedimentation method may be achieved. The difference here is that the ova and eggs float, as opposed to the formed elements 36 in the urine sample 46 that settle toward the bottom 18 of the container 10. The general approach is then the same as that described for urine sediment, except that an immiscible, barrier-forming fluid 14 having a lower specific gravity than that of the flotation solution 12 is used so that the ova and eggs may be trapped and collect at the fluidic imaging barrier 22 formed at the interface 20 between the flotation solution 12 and the barrier-forming fluid 14. Images of the ova or eggs collecting at the fluidic imaging barrier 22 may be taken in an automated fashion by an optical imaging system 2 in a similar manner to the images taken in the urine sediment example described previously, and a report of the findings may be generated with associated digital microscopy images.

Figures 13A, 13B:
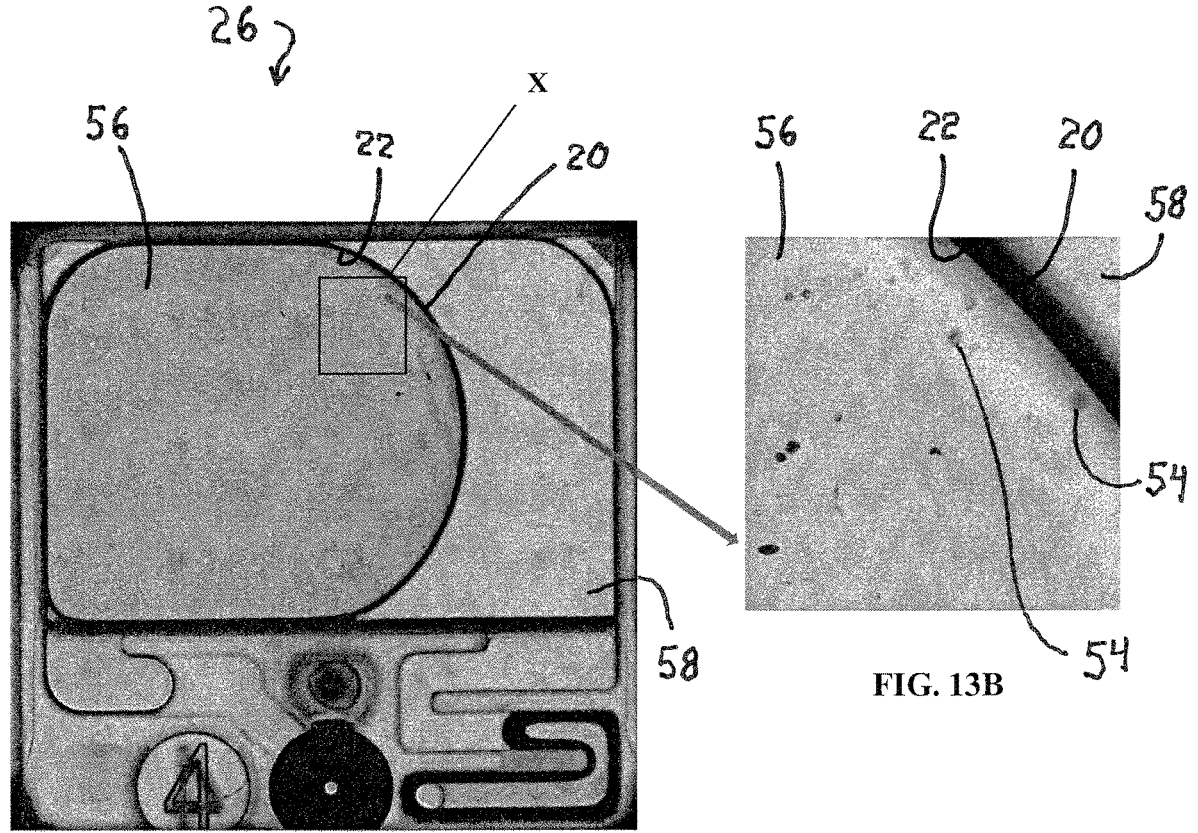
FIG. 13A is a photographic image of a container, such as that shown in FIGS. 4 and 11, used in a fecal ova analysis in which a first fluid held by the container is a zinc sulfate flotation solution containing an emulsified fecal sample and a second fluid held by the container is oleyl alcohol, both the first and second fluids being immiscible with respect to one another and having different specific gravities and forming a fluidic imaging barrier at the interface between the first and second fluids.
FIG. 13B is an enlarged photographic image of a portion of the container shown in FIG. 13A and labeled with the letter "X" in FIG. 13A, and illustrating how cells separate from the flotation solution and float toward the fluidic imaging barrier at the interface between the flotation solution (i.e., first fluid) and the oleyl alcohol (i.e., the second fluid) and collect thereat.

FIGS. 13A and 13B show microscopic images at 400× magnification of canine roundworm ova 54 in a fecal sample moving towards and concentrating at the fluidic imaging barrier 22 formed at the interface 20 of a zinc sulfate ($ZnSO_4$) flotation solution 56 (shown on the left when viewing FIG. 13A), having a specific gravity of about 1.180, and oleyl alcohol 58 having a specific gravity of between about 0.845 and about 0.855 in a SediVue™ cartridge 26. The cartridge 26 was allowed to stand uncentrifuged in a vertical disposition for about thirty (30) minutes, and then placed on its side in a horizontal disposition for imaging the ova 54 which have separated from the fecal flotation solution 56 using an optical imaging system 2 such as shown in FIG. 1A or FIG. 1B. FIG. 13B is an enlarged view of a portion of the image of the Sedivue™ cartridge 26 shown in FIG. 13A, and shows that the ova 54 do not move past the fluidic imaging barrier 22 formed at the interface 20 between the two fluids 56, 58.

Figures 14A, 14B:
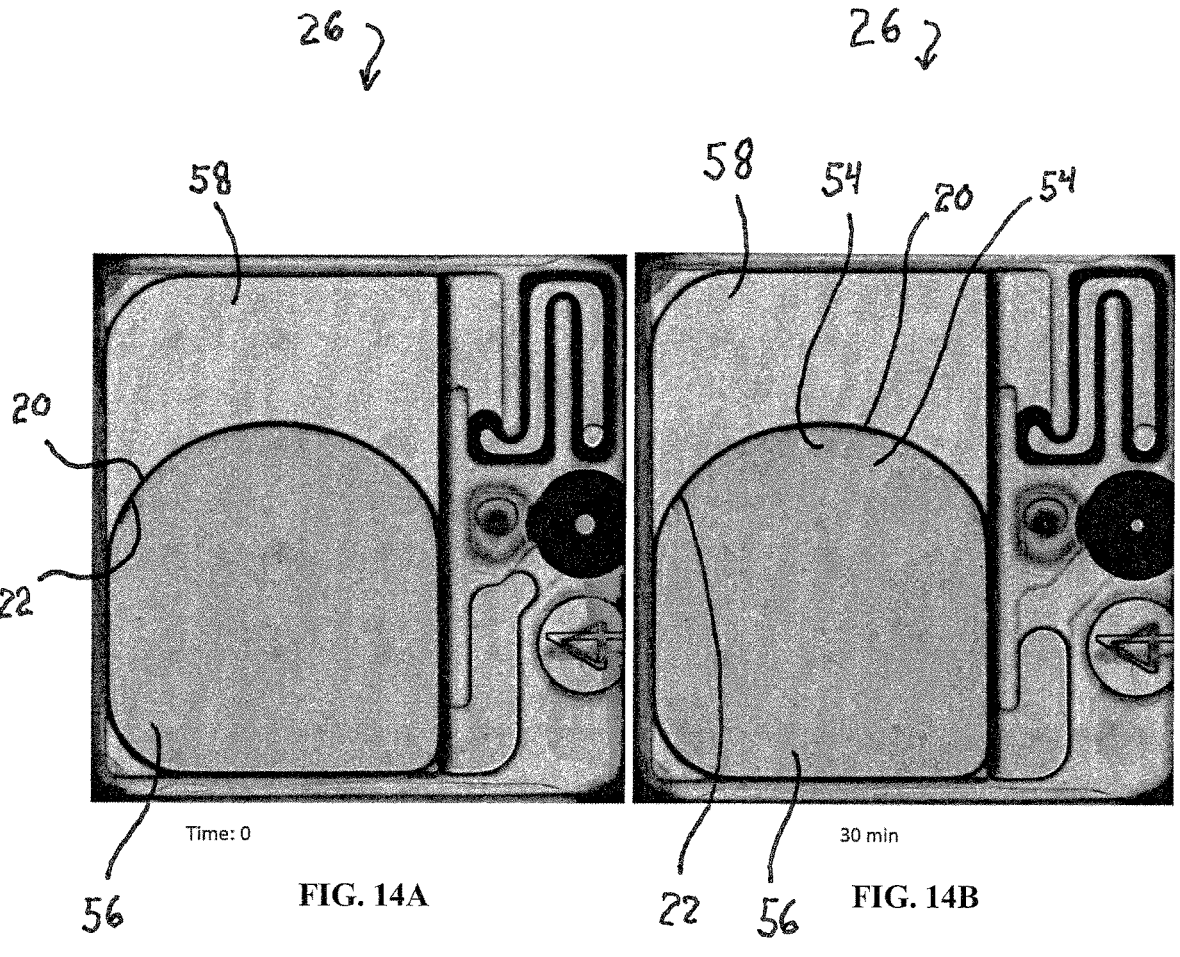
FIG. 14A is a photographic image of the container shown in FIG. 13A for fecal ova analysis, the longitudinal axis of the container being along the vertical axis, and illustrating a passive flotation method applied to the container for separating ova suspended in the flotation solution at a first relative time during application of the passive flotation method.
FIG. 14B is a photographic image of the same container shown in FIG. 14A after thirty minutes have elapsed from the time the photographic image shown in FIG. 14A was taken, and illustrating an increase in floated material at the fluidic imaging barrier situated at the interface between the flotation solution (i.e., the first fluid) and the oleyl alcohol (i.e., the second fluid).

The collection container 10, which is the SediVue™ cartridge 26 in this example, can be left oriented in a vertical disposition to support the passive gravitational floating of ova 54 to the fluidic imaging barrier 22 formed at the interface 20 between the flotation solution 56 and the immiscible barrier-forming oleyl alcohol 58. FIG. 14A is a photographic image of the SediVue™ cartridge 26 shown in FIG. 13A containing a fecal sample emulsified in a zinc sulfate flotation solution 56 and oleyl alcohol 58 as the immiscible barrier-forming fluid 14 in a passive flotation method for separating ova 54 suspended in the flotation solution 56, the image being taken at a time about when the cartridge 26 was first allowed to rest so that any ova 54 present in the fecal flotation solution 56 may separate therefrom and float upwardly in the cartridge 26. FIG. 14B is a photographic image of the same cartridge 26 shown in FIG. 14A after about thirty minutes have elapsed after the initiation of the passive flotation method applied to the cartridge 26, that is, after about thirty minutes from the time the cartridge 26 was allowed to rest so that any ova 54 present will float to and collect at the fluidic imaging barrier 22 formed at the interface 20 between the zinc sulfate flotation solution 56 and the barrier-forming oleyl alcohol 58. The cartridge 26 is in a vertical disposition at rest, meaning that the longitudinal axis of the cartridge 26 is vertical. The images of FIGS. 14A and 14B show that, after about thirty minutes of passive flotation applied to the cartridge 26, there is an increase in floated material (i.e., parasite ova 54) concentrated near the fluidic imaging barrier 22 at the interface 20 between the two fluids 56, 58, and also that the floated material (i.e., the ova 54) is not moving beyond the fluidic imaging barrier 22 at the interface 20. Artificial forces, centrifugation for example, may be applied to the cartridge 26/container 10 to increase the speed that the floated material 54 will reach the fluidic imaging barrier 22 at the interface 20 between the two fluids 56, 58 to reduce the time required for the particles 54 of interest separated from the sample fluid 56 to collect at the fluidic imaging barrier 22 for imaging by an optical imaging system 2.

The fluidic imaging barrier 22, collection container 10 and method of using the collection container 10 and fluidic barrier 22 for separating, collecting and imaging components 36 of a sample fluid 12 will now be further described.

In one embodiment, the present disclosure is directed to a fluidic imaging barrier 22 formed in a particle collection container 10 between two immiscible fluids which are received by the collection container 10, one fluid having a specific gravity which is different from that of the other fluid.

In one embodiment, the present disclosure is directed to a fluidic imaging barrier 22 formed in a particle collection container 10 between a first fluid and a second fluid which are received by the collection container 10, the first fluid and the second fluid being immiscible relative to each other, the first fluid having a first specific gravity and the second fluid having a second specific gravity, the first specific gravity of the first fluid being different from the second specific gravity of the second fluid.

In one embodiment, the present disclosure is directed to at least one fluidic imaging barrier 22 formed in a particle collection container 10 between at least two relatively immiscible fluids which are received by the collection container 10, one fluid of the at least two fluids having a first specific gravity, and another fluid of the at least two fluids having a second specific gravity which is different from the first specific gravity.

In one embodiment, the present disclosure is directed to at least a first fluidic imaging barrier 22 and a second fluidic imaging barrier 22 disposed in a particle collection container 10, the first fluidic imaging barrier 22 being formed between a first fluid and a second fluid, the second fluidic imaging barrier 22 being formed between the second fluid and a third fluid, each of the first fluid, the second fluid and the third fluid being received by the collection container 10, the first fluid being immiscible with respect to the second fluid, and the second fluid being immiscible with respect to the third fluid, the first fluid having a first specific gravity, the second fluid having a second specific gravity, and the third fluid having a third specific gravity, the first specific gravity of the first fluid being different from the second specific gravity of the second fluid, the second specific gravity of the second fluid being different from the third specific gravity of the third fluid.

In one embodiment, the present disclosure is directed to a container 10 for holding a first fluid having particles 36 suspended therein and for separating the particles 36 from the first fluid so that separated particles 36 may be imaged by an optical imaging system 2, the container 10 comprising container walls 18, 38 defining an interior cavity 42 in which the first fluid having the suspended particles 36 may be received; a second fluid received by the interior cavity 42 of the container 10, the second fluid being immiscible with respect to the first fluid, the first fluid having a first specific gravity, the second fluid having a second specific gravity and the particles 36 of the first fluid having a third specific gravity, the first specific gravity of the first fluid being different from the second specific gravity of the second fluid, the third specific gravity of the particles 36 of the first fluid being different from the first specific gravity of the first fluid and the second specific gravity of the second fluid; wherein the first fluid resides in a first location within the interior cavity 42 of the container 10, and the second fluid resides in a second location within the interior cavity 42 of the container 10 due to the second fluid being immiscible with respect to the first fluid and due to the second specific gravity of the second fluid being different from the first specific gravity of the first fluid, the first fluid residing at the first location within the interior cavity 42 of the container 10 being adjacent to and in fluidic contact with the second fluid residing at the second location along an interface 20 between the first fluid and the second fluid and defining a fluidic imaging barrier 22 thereat between the first fluid and the second fluid, the fluidic imaging barrier 22 preventing particles 36 which have separated from the first fluid from passing therethrough from the first fluid to the second fluid; and wherein the particles 36 which have separated from the first fluid will collect at the fluidic imaging barrier 22 such that the particles 36 collecting thereat may be imaged by the optical imaging system 2.

In one embodiment, the present disclosure is directed to a container 10, wherein the first fluid is a whole blood sample and wherein the particles 36 are components of the blood sample.

In one embodiment, the present disclosure is directed to a container 10, wherein the components of the blood sample are at least one of erythrocytes, leukocytes and thrombocytes.

In one embodiment, the present disclosure is directed to a container 10, wherein the first fluid is a fecal flotation solution 56 and wherein the particles 36 are at least one of parasite eggs and ova 54.

In one embodiment, the present disclosure is directed to a container 10, wherein the particles 36 separate from the first fluid and collect at the fluidic imaging barrier 22 between the first fluid and the second fluid in response to a centrifugal force applied to the container 10 and imparted on the particles 36 of the first fluid.

In one embodiment, the present disclosure is directed to a container 10, wherein the particles 36 separate from the first fluid and collect at the fluidic imaging barrier 22 between the first fluid and the second fluid in response to a gravitational force imparted on the particles 36 of the first fluid.

In one embodiment, the present disclosure is directed to a container 10, wherein the particles 36 separate from the first fluid and collect at the fluidic imaging barrier 22 between the first fluid and the second fluid in response to a flotational force imparted on the particles 36 of the first fluid.

In one embodiment, the present disclosure is directed to a container 10, wherein the container 10 includes a longitudinal axis 24 along which the interior cavity 42 of the container 10 extends; wherein the first location of the first fluid and the second location of the second fluid reside along the longitudinal axis 24 of the container 10 within the interior cavity 42 thereof; wherein the first specific gravity of the first fluid is greater than the second specific gravity of the second fluid such that the first location occupied by the first fluid within the interior cavity 42 of the container 10 is below the second location occupied by the second fluid within the interior cavity 42 of the container 10 when the longitudinal axis 24 of the container 10 is vertical; wherein the fluidic imaging barrier 22 is disposed below the second location of the second fluid and above the first location of the first fluid when the longitudinal axis 24 of the container 10 is vertical; and wherein the third specific gravity of the particles 36 of the first fluid is less than the first specific gravity of the first fluid and is greater than the second specific gravity of the second fluid such that the particles 36 separate from the first fluid and collect at the fluidic imaging barrier 22 in response to at least one of a centrifugal force, a gravitational force and a flotational force being imparted on the particles 36.

In one embodiment, the present disclosure is directed to a container 10, wherein the container 10 includes a longitudinal axis 24 along which the interior cavity 42 of the container 10 extends; wherein the first location of the first fluid and the second location of the second fluid reside along the longitudinal axis 24 of the container 10 within the interior cavity 42 thereof; wherein the second specific gravity of the second fluid is greater than the first specific gravity of the first fluid such that the second location occupied by the second fluid within the interior cavity 42 of the container 10 is below the first location occupied by the first fluid when the longitudinal axis 24 of the container 10 is vertical; wherein the fluidic imaging barrier 22 is disposed above the second location of the second fluid and below the first location of the first fluid when the longitudinal axis 24 of the container 10 is vertical; and wherein the third specific gravity of the particles 36 of the first fluid is greater than the first specific gravity of the first fluid and is less than the second specific gravity of the second fluid such that the particles 36 separate from the first fluid and collect at the fluidic imaging barrier 22 in response to at least one of a centrifugal force, a gravitational force and a flotational force being imparted on the particles 36.

In one embodiment, the present disclosure is directed to a collection container 10 for use in separating particles 36 of interest suspended in a sample fluid 12 and for collecting separated particles 36 of interest in a concentrated volume of the container 10, the sample fluid 12 having a specific gravity associated therewith, the particles 36 of interest suspended in the sample fluid 12 having specific gravities associated therewith, the specific gravities of the particles 36 of interest being different from the specific gravity of the sample fluid 12, the collection container 10 comprising container walls 18, 38, the container walls 18, 38 defining an interior cavity 42 of the collection container 10 for receiving and holding the sample fluid 12 having the particles 36 of interest suspended therein; and at least one barrier-forming fluid 14 received by the interior cavity 42 of the collection container 10, the at least one barrier-forming fluid 14 being immiscible with the sample fluid 12 when the sample fluid 12 is received by the interior cavity 42 of the collection container 10 and having a specific gravity associated therewith, the specific gravity of the at least one barrier-forming fluid 14 being different from the specific gravity of the sample fluid 12 and the specific gravities of the particles 36 of interest suspended in the sample fluid 12, the at least one barrier-forming fluid 14 being disposed in the interior cavity 42 of the collection container 10 adjacent to and in contact with the sample fluid 12 when the sample fluid 12 is received by the interior cavity 42 of the collection container 10 at an interface 20 between the sample fluid 12 and the at least one barrier-forming fluid 14 and forming a fluidic barrier 22 at the interface 20 between the sample fluid 12 and the at least one barrier-forming fluid 14; whereby, when the sample fluid 12 having the particles 36 suspended therein is received by the interior cavity 42 of the collection container 10, the particles 36 of interest will separate from the sample fluid 12 in which the particles 36 of interest were suspended and move to and collect in a concentrated volume at the fluidic barrier 22 formed at the interface 20 between the sample fluid 12 and the at least one barrier-forming fluid 14.

In one embodiment, the present disclosure is directed to a collection container 10, wherein the specific gravities of the particles 36 of interest suspended in the sample fluid 12 are greater than the specific gravity of the sample fluid 12; wherein the specific gravity of the at least one barrier-forming fluid 14 is greater than the specific gravity of the sample fluid 12; and wherein the specific gravity of the at least one barrier-forming fluid 14 is greater than the specific gravities of the particles 36 of interest suspended in the sample fluid 12.

In one embodiment, the present disclosure is directed to a collection container 10, wherein the collection container 10 has a longitudinal axis 24 associated therewith; and wherein, when the sample fluid 12 having the particles 36 of interest suspended therein is received by the interior cavity 42 of the collection container 10, the at least one barrier-forming fluid 14 will assume a position below the sample fluid 12 within the interior cavity 42 of the collection container 10 when the collection container 10 is viewed as being oriented such that the longitudinal axis 24 thereof is vertical.

In one embodiment, the present disclosure is directed to a collection container 10, wherein the specific gravities of the particles 36 of interest suspended in the sample fluid 12 are less than the specific gravity of the sample fluid 12; wherein the specific gravity of the at least one barrier-forming fluid 14 is less than the specific gravity of the sample fluid 12; and wherein the specific gravity of the at least one barrier-forming fluid 14 is less than the specific gravities of the particles 36 of interest suspended in the sample fluid 12.

In one embodiment, the present disclosure is directed to a collection container 10, wherein the collection container 10 has a longitudinal axis 24 associated therewith; and wherein, when the sample fluid 12 having the particles 36 of interest suspended therein is received by the interior cavity 42 of the collection container 10, the at least one barrier-forming fluid 14 will assume a position above the sample fluid 12 within the interior cavity 42 of the collection container 10 when the collection container 10 is viewed as being oriented such that the longitudinal axis 24 thereof is vertical.

In one embodiment, the present disclosure is directed to a collection container 10 for use in separating particles 36 of interest suspended in a fluid and for collecting separated particles 36 of interest in a concentrated volume of the container 10, the collection container 10 comprising container walls 18, 38, the container walls 18, 38 defining an interior cavity 42 of the collection container 10; a sample fluid 12 disposed within the interior cavity 42 of the collection container 10 and having the particles 36 of interest suspended therein, the sample fluid 12 having a specific gravity associated therewith, the particles 36 of interest suspended in the sample fluid 12 having specific gravities associated therewith, the specific gravities of the particles 36 of interest being different from the specific gravity of the sample fluid 12; a first barrier-forming fluid 14 disposed within the interior cavity 42 of the collection container 10, the first barrier-forming fluid 14 being immiscible with respect to the sample fluid 12 and having a specific gravity associated therewith, the specific gravity of the first barrier-forming fluid 14 being different from the specific gravity of the sample fluid 12 and the specific gravities of the particles 36 of interest suspended in the sample fluid 12, the first barrier-forming fluid 14 being disposed in the interior cavity 42 of the collection container 10 adjacent to and in contact with the sample fluid 12 at an interface 20 between the sample fluid 12 and the first barrier-forming fluid 14; and a first fluidic barrier 22a disposed within the interior cavity 42 of the collection container 10 at the interface 20 between the sample fluid 12 and the first barrier-forming fluid 14; whereby the particles 36 of interest will separate from the sample fluid 12 in which the particles 36 of interest were suspended and move to and collect in a concentrated volume in proximity to the first fluidic barrier 22a disposed at the interface 20 between the sample fluid 12 and the first barrier-forming fluid 14.

In one embodiment, the present disclosure is directed to a collection container 10, wherein the specific gravities of the particles 36 of interest suspended in the sample fluid 12 are greater than the specific gravity of the sample fluid 12; wherein the specific gravity of the first barrier-forming fluid 14 is greater than the specific gravity of the sample fluid 12; and wherein the specific gravity of the first barrier-forming fluid 14 is greater than the specific gravities of the particles 36 of interest suspended in the sample fluid 12, such as in the embodiment shown in FIGS. 6A and 6B.

In one embodiment, the present disclosure is directed to a collection container 10, wherein the collection container 10 has a longitudinal axis 24 associated therewith; and wherein the first barrier-forming fluid 14 is disposed in a position below the sample fluid 12 within the interior cavity 42 of the collection container 10 when the collection container 10 is viewed as being oriented such that the longitudinal axis 24 thereof is vertical, such as in the embodiment shown in FIGS. 6A and 6B.

In one embodiment, the present disclosure is directed to a collection container 10, wherein the specific gravities of the particles 36 of interest suspended in the sample fluid 12 are less than the specific gravity of the sample fluid 12; wherein the specific gravity of the first barrier-forming fluid 14 is less than the specific gravity of the sample fluid 12; and wherein the specific gravity of the first barrier-forming fluid 14 is less than the specific gravities of the particles 36 of interest suspended in the sample fluid 12, such as in the embodiment shown in FIGS. 5A and 5B.

In one embodiment, the present disclosure is directed to a collection container 10, wherein the collection container 10 has a longitudinal axis 24 associated therewith; and wherein the first barrier-forming fluid 14 is disposed in a position above the sample fluid 12 within the interior cavity 42 of the collection container 10 when the collection container 10 is viewed as being oriented such that the longitudinal axis 24 thereof is vertical, such as in the embodiment shown in FIGS. 5A and 5B.

In one embodiment, such as in the embodiment shown in FIGS. 7A and 7B, the present disclosure is directed to a collection container 10 for use in separating particles 36 of interest suspended in a fluid and for collecting separated particles 36 of interest in a concentrated volume of the container 10, the collection container 10 comprising container walls 18, 38, the container walls 18, 38 defining an interior cavity 42 of the collection container 10; a sample fluid 12 disposed within the interior cavity 42 of the collection container 10 and having first particles 36a of interest suspended therein and second particles 36b of interest suspended therein, the sample fluid 12 having a specific gravity associated therewith, the first particles 36a of interest suspended in the sample fluid 12 having first specific gravities associated therewith, the second particles 36b of interest suspended in the sample fluid 12 having second specific gravities associated therewith, the first specific gravities of the first particles 36a of interest being different from the specific gravity of the sample fluid 12, the second specific gravities of the second particles 36b of interest being different from the specific gravity of the sample fluid 12, the first specific gravities of the first particles 36a of interest being different from the second specific gravities of the second particles 36b of interest; a first barrier-forming fluid 14 disposed within the interior cavity 42 of the collection container 10, the first barrier-forming fluid 14 being immiscible with respect to the sample fluid 12 and having a specific gravity associated therewith, the specific gravity of the first barrier-forming fluid 14 being different from the specific gravity of the sample fluid 12, the specific gravity of the first barrier-forming fluid 14 being different from the first specific gravities of the first particles 36a of interest suspended in the sample fluid 12, the specific gravity of the first barrier-forming fluid 14 being different from the second specific gravities of the second particles 36b of interest suspended in the sample fluid 12, the first barrier-forming fluid 14 being disposed in the interior cavity 42 of the collection container 10 adjacent to and in contact with the sample fluid 12 at an interface 20 between the sample fluid 12 and the first barrier-forming fluid 14; a first fluidic barrier 22a disposed within the interior cavity 42 of the collection container 10 at the interface 20 between the sample fluid 12 and the first barrier-forming fluid 14; a second barrier-forming fluid 16 disposed within the interior cavity 42 of the collection container 10, the second barrier-forming fluid 16 being immiscible with respect to at least the first barrier-forming fluid 14 and having a specific gravity associated therewith, the specific gravity of the second barrier-forming fluid 16 being different from the specific gravity of the sample fluid 12, the specific gravity of the second barrier-forming fluid 16 being different from the specific gravity of the first barrier-forming fluid 14, the specific gravity of the second barrier-forming fluid 16 being different from the first specific gravities of the first particles 36a of interest suspended in the sample fluid 12, the specific gravity of the second barrier-forming fluid 16 being different from the second specific gravities of the second particles 36b of interest suspended in the sample fluid 12, the second barrier-forming fluid 16 being disposed in the interior cavity 42 of the collection container 10 adjacent to and in contact with the first barrier-forming fluid 14 at an interface 20 between the first barrier-forming fluid 14 and the second barrier-forming fluid 16; a second fluidic barrier 22b disposed within the interior cavity 42 of the collection container 10 at the interface 20 between the first barrier-forming fluid 14 and the second barrier-forming fluid 16; whereby the first particles 36*a* of interest will separate from the sample fluid 12 in which the first particles 36*a* of interest were suspended and move to and collect in a concentrated volume in proximity to the first fluidic barrier 22*a* disposed at the interface 20 between the sample fluid 12 and the first barrier-forming fluid 14; and whereby the second particles 36*b* of interest will separate from the sample fluid 12 in which the second particles 36*b* of interest were suspended and move to and collect in a concentrated volume in proximity to the second fluidic barrier 22*b* disposed at the interface 20 between the first barrier-forming fluid 14 and the second barrier-forming fluid 16.

In one embodiment, such as in the embodiment shown in FIGS. 7A and 7B, the present disclosure is directed to a collection container 10, wherein the first specific gravities of the first particles 36*a* of interest suspended in the sample fluid 12 are less than the specific gravity of the sample fluid 12; wherein the second specific gravities of the second particles 36*b* of interest suspended in the sample fluid 12 are less than the specific gravity of the sample fluid 12; wherein the first specific gravities of the first particles 36*a* of interest suspended in the sample fluid 12 are greater than the second specific gravities of the second particles 36*b* of interest suspended in the sample fluid 12; wherein the specific gravity of the first barrier-forming fluid 14 is less than the specific gravity of the sample fluid 12; wherein the specific gravity of the first barrier-forming fluid 14 is greater than the specific gravity of the second barrier-forming fluid 16; wherein the specific gravity of the first barrier-forming fluid 14 is less than the first specific gravities of the first particles 36*a* of interest suspended in the sample fluid 12; wherein the specific gravity of the first barrier-forming fluid 14 is greater than the second specific gravities of the second particles 36*b* of interest suspended in the sample fluid 12; and wherein the specific gravity of the second barrier-forming fluid 16 is less than the second specific gravities of the second particles 36*b* of interest suspended in the sample fluid 12.

In one embodiment, such as in the embodiment shown in FIGS. 7A and 7B, the present disclosure is directed to a collection container 10, wherein the collection container 10 has a longitudinal axis 24 associated therewith; wherein the first barrier-forming fluid 14 is disposed in a position above the sample fluid 12 within the interior cavity 42 of the collection container 10 when the collection container 10 is viewed as being oriented such that the longitudinal axis 24 thereof is vertical; and wherein the second barrier-forming fluid 16 is disposed in a position above the first barrier-forming fluid 14 within the interior cavity 42 of the collection container 10 when the collection container 10 is viewed as being oriented such that the longitudinal axis 24 thereof is vertical.

In one embodiment, such as in the embodiment shown in FIGS. 8A and 8B, the present disclosure is directed to a collection container 10 for use in separating particles 36 of interest suspended in a fluid and for collecting separated particles 36 of interest in a concentrated volume of the container 10, the collection container 10 comprising container walls 18, 38, the container walls 18, 38 defining an interior cavity 42 of the collection container 10; a sample fluid 12 disposed within the interior cavity 42 of the collection container 10 and having first particles 36*a* of interest suspended therein and second particles 36*b* of interest suspended therein, the sample fluid 12 having a specific gravity associated therewith, the first particles 36*a* of interest suspended in the sample fluid 12 having first specific gravities associated therewith, the second particles 36*b* of interest suspended in the sample fluid 12 having second specific gravities associated therewith, the first specific gravities of the first particles 36*a* of interest being different from the specific gravity of the sample fluid 12, the second specific gravities of the second particles 36*b* of interest being different from the specific gravity of the sample fluid 12, the first specific gravities of the first particles 36*a* of interest being different from the second specific gravities of the second particles 36*b* of interest; a first barrier-forming fluid 14 disposed within the interior cavity 42 of the collection container 10; a second barrier-forming fluid 16 disposed within the interior cavity 42 of the collection container 10, the second barrier-forming fluid 16 being immiscible with respect to the sample fluid 12 and having a specific gravity associated therewith, the specific gravity of the second barrier-forming fluid 16 being different from the specific gravity of the sample fluid 12, the specific gravity of the second barrier-forming fluid 16 being different from the first specific gravities of the first particles 36*a* of interest suspended in the sample fluid 12, the specific gravity of the second barrier-forming fluid 16 being different from the second specific gravities of the second particles 36*b* of interest suspended in the sample fluid 12, the second barrier-forming fluid 16 being disposed in the interior cavity 42 of the collection container 10 adjacent to and in contact with the sample fluid 12 at an interface 20 between the sample fluid 12 and the second barrier-forming fluid 16, the first barrier-forming fluid 14 being immiscible with respect to at least the second barrier-forming fluid 16 and having a specific gravity associated therewith, the specific gravity of the first barrier-forming fluid 14 being different from the specific gravity of the sample fluid 12, the specific gravity of the first barrier-forming fluid 14 being different from the specific gravity of the second barrier-forming fluid 16, the specific gravity of the first barrier-forming fluid 14 being different from the first specific gravities of the first particles 36*a* of interest suspended in the sample fluid 12, the specific gravity of the first barrier-forming fluid 14 being different from the second specific gravities of the second particles 36*b* of interest suspended in the sample fluid 12, the first barrier-forming fluid 14 being disposed in the interior cavity 42 of the collection container 10 adjacent to and in contact with the second barrier-forming fluid 16 at an interface 20 between the second barrier-forming fluid 16 and the first barrier-forming fluid 14; a first fluidic barrier 22*a* disposed within the interior cavity 42 of the collection container 10 at the interface 20 between the second barrier-forming fluid 16 and the first barrier-forming fluid 14; and a second fluidic barrier 22*b* disposed within the interior cavity 42 of the collection container 10 at the interface 20 between the sample fluid 12 and the second barrier-forming fluid 16; whereby the first particles 36*a* of interest will separate from the sample fluid 12 in which the first particles 36*a* of interest were suspended and move to and collect in a concentrated volume in proximity to the first fluidic barrier 22*a* disposed at the interface 20 between the first barrier-forming fluid 14 and the second barrier-forming fluid 16; and whereby the second particles 36*b* of interest will separate from the sample fluid 12 in which the second particles 36*b* of interest were suspended and move to and collect in a concentrated volume in proximity to the second fluidic barrier 22*b* disposed at the interface 20 between the sample fluid 12 and the second barrier-forming fluid 16.

In one embodiment, such as in the embodiment shown in FIGS. 8A and 8B, the present disclosure is directed to a collection container 10, wherein the first specific gravities of the first particles 36a of interest suspended in the sample fluid 12 are greater than the specific gravity of the sample fluid 12; wherein the second specific gravities of the second particles 36b of interest suspended in the sample fluid 12 are greater than the specific gravity of the sample fluid 12; wherein the first specific gravities of the first particles 36a of interest suspended in the sample fluid 12 are greater than the second specific gravities of the second particles 36b of interest suspended in the sample fluid 12; wherein the specific gravity of the second barrier-forming fluid 16 is greater than the specific gravity of the sample fluid 12; wherein the specific gravity of the first barrier-forming fluid 14 is greater than the specific gravity of the second barrier-forming fluid 16; wherein the specific gravity of the first barrier-forming fluid 14 is greater than the first specific gravities of the first particles 36a of interest suspended in the sample fluid 12; wherein the specific gravity of the first barrier-forming fluid 14 is greater than the second specific gravities of the second particles 36b of interest suspended in the sample fluid 12; wherein the specific gravity of the second barrier-forming fluid 16 is greater than the second specific gravities of the second particles 36b of interest suspended in the sample fluid 12; and wherein the specific gravity of the second barrier-forming fluid 16 is less than the first specific gravities of the first particles 36a of interest suspended in the sample fluid 12.

In one embodiment, such as in the embodiment shown in FIGS. 8A and 8B, the present disclosure is directed to a collection container 10, wherein the collection container 10 has a longitudinal axis 24 associated therewith; wherein the second barrier-forming fluid 16 is disposed in a position below the sample fluid 12 within the interior cavity 42 of the collection container 10 when the collection container 10 is viewed as being oriented such that the longitudinal axis 24 thereof is vertical; and wherein the first barrier-forming fluid 14 is disposed in a position below the second barrier-forming fluid 16 within the interior cavity 42 of the collection container 10 when the collection container 10 is viewed as being oriented such that the longitudinal axis 24 thereof is vertical.

In one embodiment, such as in the embodiment shown in FIGS. 9A and 9B, the present disclosure is directed to a collection container 10 for use in separating particles 36 of interest suspended in a fluid and for collecting separated particles 36 of interest in a concentrated volume of the container 10, the collection container 10 comprising container walls 18, 38, the container walls 18, 38 defining an interior cavity 42 of the collection container 10; a sample fluid 12 disposed within the interior cavity 42 of the collection container 10 and having first particles 36a of interest suspended therein and second particles 36b of interest suspended therein, the sample fluid 12 having a specific gravity associated therewith, the first particles 36a of interest suspended in the sample fluid 12 having first specific gravities associated therewith, the second particles 36b of interest suspended in the sample fluid 12 having second specific gravities associated therewith, the first specific gravities of the first particles 36a of interest being different from the specific gravity of the sample fluid 12, the second specific gravities of the second particles 36b of interest being different from the specific gravity of the sample fluid 12, the first specific gravities of the first particles 36a of interest being different from the second specific gravities of the second particles 36b of interest; a first barrier-forming fluid 14 disposed within the interior cavity 42 of the collection container 10, the first barrier-forming fluid 14 being immiscible with respect to the sample fluid 12 and having a specific gravity associated therewith, the specific gravity of the first barrier-forming fluid 14 being different from the specific gravity of the sample fluid 12, the specific gravity of the first barrier-forming fluid 14 being different from the first specific gravities of the first particles 36a of interest suspended in the sample fluid 12, the specific gravity of the first barrier-forming fluid 14 being different from the second specific gravities of the second particles 36b of interest suspended in the sample fluid 12, the first barrier-forming fluid 14 being disposed in the interior cavity 42 of the collection container 10 adjacent to and in contact with the sample fluid 12 at an interface 20 between the first barrier-forming fluid 14 and the sample fluid 12; a first fluidic barrier 22a disposed within the interior cavity 42 of the collection container 10 at the interface 20 between the sample fluid 12 and the first barrier-forming fluid 14; a second barrier-forming fluid 16 disposed within the interior cavity 42 of the collection container 10, the second barrier-forming fluid 16 being immiscible with respect to the sample fluid 12 and having a specific gravity associated therewith, the specific gravity of the second barrier-forming fluid 16 being different from the specific gravity of the sample fluid 12, the specific gravity of the second barrier-forming fluid 16 being different from the first specific gravities of the first particles 36a of interest suspended in the sample fluid 12, the specific gravity of the second barrier-forming fluid 16 being different from the second specific gravities of the second particles 36b of interest suspended in the sample fluid 12, the second barrier-forming fluid 16 being disposed in the interior cavity 42 of the collection container 10 adjacent to and in contact with the sample fluid 12 at an interface 20 between the sample fluid 12 and the second barrier-forming fluid 16; a second fluidic barrier 22b disposed within the interior cavity 42 of the collection container 10 at the interface 20 between the sample fluid 12 and the second barrier-forming fluid 16; whereby the first particles 36a of interest will separate from the sample fluid 12 in which the first particles 36a of interest were suspended and move to and collect in a concentrated volume in proximity to the first fluidic barrier 22a disposed at the interface 20 between the sample fluid 12 and the first barrier-forming fluid 14; and whereby the second particles 36b of interest will separate from the sample fluid 12 in which the second particles 36b of interest were suspended and move to and collect in a concentrated volume in proximity to the second fluidic barrier 22b disposed at the interface 20 between the sample fluid 12 and the second barrier-forming fluid 16.

In one embodiment, such as in the embodiment shown in FIGS. 9A and 9B, the present disclosure is directed to a collection container 10, wherein the first specific gravities of the first particles 36a of interest suspended in the sample fluid 12 are greater than the specific gravity of the sample fluid 12; wherein the second specific gravities of the second particles 36b of interest suspended in the sample fluid 12 are less than the specific gravity of the sample fluid 12; wherein the first specific gravities of the first particles 36a of interest suspended in the sample fluid 12 are greater than the second specific gravities of the second particles 36b of interest suspended in the sample fluid 12; wherein the specific gravity of the first barrier-forming fluid 14 is greater than the specific gravity of the sample fluid 12; wherein the specific gravity of the first barrier-forming fluid 14 is greater than the specific gravity of the second barrier-forming fluid 16; wherein the specific gravity of the first barrier-forming fluid 14 is greater than the first specific gravities of the first particles 36a of interest suspended in the sample fluid 12; wherein the specific gravity of the first barrier-forming fluid 14 is greater than the second specific gravities of the second particles 36b of interest suspended in the sample fluid 12; wherein the specific gravity of the second barrier-forming fluid 16 is less than the specific gravity of the sample fluid 12; and wherein the specific gravity of the second barrier-forming fluid 16 is less than the second specific gravities of the second particles 36b of interest suspended in the sample fluid 12.

In one embodiment, such as in the embodiment shown in FIGS. 9A and 9B, the present disclosure is directed to a collection container 10, wherein the collection container 10 has a longitudinal axis 24 associated therewith; wherein the first barrier-forming fluid 14 is disposed in a position below the sample fluid 12 within the interior cavity 42 of the collection container 10 when the collection container 10 is viewed as being oriented such that the longitudinal axis 24 thereof is vertical; and wherein the second barrier-forming fluid 16 is disposed in a position above the sample fluid 12 within the interior cavity 42 of the collection container 10 when the collection container 10 is viewed as being oriented such that the longitudinal axis 24 thereof is vertical.

In one embodiment, the present disclosure is directed to a method of forming a fluidic barrier 22 in a container 10, the container 10 having walls defining an interior cavity 42 for holding fluids, the method comprising the steps of adding a first fluid to the interior cavity 42 of the container 10, the first fluid having a first specific gravity associated therewith; and adding a second fluid to the interior cavity 42 of the container 10 before or after the first fluid is added to the interior cavity 42 of the container 10, the second fluid having a second specific gravity associated therewith, the second specific gravity of the second fluid being different from the first specific gravity of the first fluid, the first fluid and the second fluid being immiscible with respect to each other such that the second fluid resides within the interior cavity 42 of the container 10 adjacent to the first fluid and contacts the first fluid at an interface 20 therebetween to form the fluidic barrier 22 thereat.

In one embodiment, the present disclosure is directed to a method of collecting particles 36 of interest in a collection container 10, the collection container 10 having walls defining an interior cavity 42 for receiving fluids, the method comprising the steps of adding a first fluid to the interior cavity 42 of the collection container 10, the first fluid having particles 36 of interest suspended therein, the first fluid having a specific gravity associated therewith, the particles 36 of interest suspended in the first fluid having specific gravities associated therewith, the specific gravities of the particles 36 of interest being different from the specific gravity of the first fluid; adding a second fluid to the interior cavity 42 of the collection container 10 before or after the first fluid is added to the interior cavity 42 of the collection container 10, the second fluid having a specific gravity associated therewith, the specific gravity of the second fluid being different from the specific gravity of the first fluid, the specific gravity of the second fluid being different from the specific gravities of the particles 36 of interest suspended in the first fluid, the second fluid being immiscible with respect to the first fluid, the second fluid residing within the interior cavity 42 of the collection container 10 at a position therein adjacent to and in contact with the first fluid at an interface 20 between the first fluid and the second fluid, the first fluid having the particles 36 of interest suspended therein and the immiscible second fluid forming a fluidic barrier 22 at the interface 20 between the first fluid and the second fluid; and passively or actively causing the particles 36 of interest suspended in the first fluid to separate from the first fluid, the particles 36 of interest moving in the interior cavity 42 of the collection container 10 toward the fluidic barrier 22 at the interface 20 between the first fluid and the second fluid, the particles 36 of interest, separated from the first fluid, collecting at a location within the interior cavity 42 of the collection container 10 in proximity to the fluidic barrier 22.

In one embodiment, the present disclosure is directed to a method, wherein the step of passively or actively causing the particles 36 of interest to separate from the first fluid includes the step of centrifuging the collection container 10 to impart a centrifugal force on the particles 36 of interest suspended in the first fluid, whereupon the particles 36 of interest will move toward and collect at the location in the interior cavity 42 of the collection container 10 in proximity to the fluidic barrier 22.

In one embodiment, the present disclosure is directed to a method, wherein the step of passively or actively causing the particles 36 of interest to separate from the first fluid includes the step of allowing the collection container 10 to rest undisturbed for a sufficient period of time to impart one of a gravitational force and a flotational force on the particles 36 of interest suspended in the first fluid, whereupon the particles 36 of interest will move toward and collect at the location in the interior cavity 42 of the collection container 10 in proximity to the fluidic barrier 22.

In one embodiment, the present disclosure is directed to a passive flotation method for separating particles 36 from a sample of matter and concentrating the particles 36 in a predefined area of a collection container 10, which comprises the steps of mixing in the collection container 10 the sample of matter containing the particles 36 with a flotation solution 56 having a predetermined specific gravity such that the particles 36 are suspended in the flotation solution 56, the collection container 10 including walls defining an interior cavity 42 for holding the flotation solution 56 having the particles 36 suspended therein; adding a barrier-forming fluid 14 to the interior cavity 42 of the collection container 10 such that the barrier-forming fluid 14 resides on top of the flotation solution 56, the barrier-forming fluid 14 being immiscible with the flotation solution 56 and having a specific gravity which is less than the specific gravity of the flotation solution 56 and the specific gravities of the particles 36 suspended in the flotation solution 56, the barrier-forming fluid 14 being in contact with the flotation solution 56 at an interface 20 between the flotation solution 56 and the barrier-forming fluid 14, the flotation solution 56 and the immiscible barrier-forming fluid 14 forming a fluidic barrier 22 within the interior cavity 42 of the collection container 10 at the interface 20 between the flotation solution 56 and the barrier-forming fluid 14; and allowing the flotation solution 56 having the particles 36 suspended therein within the interior cavity 42 of the collection container 10 to rest for a sufficient period of time so that particles 36 suspended in the flotation solution 56 having specific gravities which are less than the specific gravity of the flotation solution 56 will separate therefrom and rise in the interior cavity 42 of the collection container 10 to form a concentrated quantity of separated particles 36 accumulating at a location within the interior cavity 42 of the collection container 10 in proximity to the fluidic barrier 22.

In one embodiment, the present disclosure is directed to a passive flotation method, which includes the step of optically imaging the concentrated quantity of separated particles 36 accumulating at the location within the interior cavity 42 of the collection container 10 in proximity to the fluidic barrier 22 by an optical imaging system 2.

In one embodiment, the present disclosure is directed to a passive flotation method, wherein the flotation solution 56 is zinc sulfate; and wherein the barrier-forming fluid 14 is oleyl alcohol 58.

In one embodiment, the present disclosure is directed to an active particle separation method for separating particles 36 from a sample of matter and concentrating the particles 36 in a predefined area of a collection container 10, which comprises the steps of mixing in the collection container 10 the sample of matter containing the particles 36 with a flotation solution 56 having a predetermined specific gravity such that the particles 36 are suspended in the flotation solution 56, the collection container 10 including walls defining an interior cavity 42 for holding the flotation solution 56 having the particles 36 suspended therein; adding a barrier-forming fluid 14 to the interior cavity 42 of the collection container 10 such that the barrier-forming fluid 14 resides on top of the flotation solution 56, the barrier-forming fluid 14 being immiscible with the flotation solution 56 and having a specific gravity which is less than the specific gravity of the flotation solution 56 and the specific gravities of the particles 36 suspended in the flotation solution 56, the barrier-forming fluid 14 being in contact with the flotation solution 56 at an interface 20 between the flotation solution 56 and the barrier-forming fluid 14, the flotation solution 56 and the immiscible barrier-forming fluid 14 forming a fluidic barrier 22 within the interior cavity 42 of the collection container 10 at the interface 20 between the flotation solution 56 and the barrier-forming fluid 14; and centrifuging the collection container 10 holding flotation solution 56 having the particles 36 suspended therein and the barrier-forming fluid 14 within the interior cavity 42 of the collection container 10 for a sufficient period of time so that particles 36 suspended in the flotation solution 56 having specific gravities which are less than the specific gravity of the flotation solution 56 will separate therefrom and will be centrifugally forced to move in the interior cavity 42 of the collection container 10 to form a concentrated quantity of separated particles 36 accumulating at a location within the interior cavity 42 of the collection container 10 in proximity to the fluidic barrier 22.

In one embodiment, the present disclosure is directed to an active particle separation method, which includes the step of optically imaging the concentrated quantity of separated particles 36 accumulating at the location within the interior cavity 42 of the collection container 10 in proximity to the fluidic barrier 22 by an optical imaging system 2.

In one embodiment, the present disclosure is directed to an active particle separation method, wherein the flotation solution 56 is zinc sulfate; and wherein the barrier-forming fluid 14 is oleyl alcohol 58.

In one embodiment, the present disclosure is directed to a passive urine sedimentation method for separating particles 36 of interest suspended in a urine sample 46 and concentrating the particles 36 in a predefined area of a collection container 10, the collection container 10 having walls defining an interior cavity 42, the method comprising the steps of adding a sucrose solution 52 as a barrier-forming fluid 14 to the interior cavity 42 of the collection container 10; adding the urine sample 46 having the particles 36 of interest suspended therein to the interior cavity 42 of the collection container 10 so that the urine sample 46 resides in the interior cavity 42 of the collection container 10 above the sucrose solution 52, the urine sample 46 having a specific gravity associated therewith, the particles 36 of interest suspended in the urine sample 46 having specific gravities which are greater than the specific gravity of the urine sample 46, the sucrose solution 52 being immiscible with the urine sample 46 and having a specific gravity which is greater than the specific gravity of the urine sample 46 and is greater than the specific gravities of the particles 36 of interest suspended in the urine sample 46, the sucrose solution 52 being in contact with the urine sample 46 at an interface 20 between the urine sample 46 and the sucrose solution 52, the urine sample 46 and the immiscible sucrose solution 52 forming a fluidic barrier 22 within the interior cavity 42 of the collection container 10 at the interface 20 between the urine sample 46 and the sucrose solution 52; and allowing the urine sample 46 having the particles 36 suspended therein within the interior cavity 42 of the collection container 10 to rest for a sufficient period of time so that particles 36 suspended in the urine sample 46 having specific gravities which are greater than the specific gravity of the urine sample 46 will separate therefrom and gravitate in the interior cavity 42 of the collection container 10 toward the fluidic barrier 22 to form a concentrated quantity of separated particles 36 accumulating at a location within the interior cavity 42 of the collection container 10 in proximity to the fluidic barrier 22.

In one embodiment, the present disclosure is directed to an active urine sedimentation method for separating particles 36 of interest suspended in a urine sample 46 and concentrating the particles 36 in a predefined area of a collection container 10, the collection container 10 having walls defining an interior cavity 42, the method comprising the steps of adding a sucrose solution 52 as a barrier-forming fluid 14 to the interior cavity 42 of the collection container 10; adding the urine sample 46 having the particles 36 of interest suspended therein to the interior cavity 42 of the collection container 10 so that the urine sample 46 resides in the interior cavity 42 of the collection container 10 above the sucrose solution 52, the urine sample 46 having a specific gravity associated therewith, the particles 36 of interest suspended in the urine sample 46 having specific gravities which are greater than the specific gravity of the urine sample 46, the sucrose solution 52 being immiscible with the urine sample 46 and having a specific gravity which is greater than the specific gravity of the urine sample 46 and is greater than the specific gravities of the particles 36 of interest suspended in the urine sample 46, the sucrose solution 52 being in contact with the urine sample 46 at an interface 20 between the urine sample 46 and the sucrose solution 52, the urine sample 46 and the immiscible sucrose solution 52 forming a fluidic barrier 22 within the interior cavity 42 of the collection container 10 at the interface 20 between the urine sample 46 and the sucrose solution 52; and centrifuging the collection container 10 holding the urine sample 46 having the particles 36 suspended therein and the sucrose solution 52 within the interior cavity 42 of the collection container 10 for a sufficient period of time so that particles 36 suspended in the urine sample 46 having specific gravities which are greater than the specific gravity of the urine sample 46 will separate therefrom and will be centrifugally forced to move in the interior cavity 42 of the collection container 10 to form a concentrated quantity of separated particles 36 accumulating at a location within the interior cavity 42 of the collection container 10 in proximity to the fluidic barrier 22.

Although illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method for separating particles from a sample of matter and concentrating the particles in a predefined area of a collection container, which comprises the steps of:

mixing in the collection container the sample of matter containing the particles with a flotation solution having a predetermined specific gravity such that the particles are suspended in the flotation solution, the collection container including walls defining an interior cavity for holding the flotation solution having the particles suspended therein;

adding a barrier-forming fluid to the interior cavity of the collection container such that the barrier-forming fluid resides on top of the flotation solution, the barrier-forming fluid being immiscible with the flotation solution and having a specific gravity which is less than the specific gravity of the flotation solution and specific gravities of the particles suspended in the flotation solution, the barrier-forming fluid being in contact with the flotation solution at an interface between the flotation solution and the barrier-forming fluid, the flotation solution and the immiscible barrier-forming fluid forming a fluidic barrier within the interior cavity of the collection container at the interface between the flotation solution and the barrier-forming fluid; and allowing the flotation solution having the particles suspended therein within the interior cavity of the collection container to rest so that particles suspended in the flotation solution having specific gravities which are less than the specific gravity of the flotation solution separate therefrom and rise in the interior cavity of the collection container to form a concentrated quantity of separated particles accumulating at a location within the interior cavity of the collection container in proximity to the fluidic barrier.

2. A method as defined by claim 1, which further comprises the step of: optically imaging the concentrated quantity of separated particles accumulating at the location within the interior cavity of the collection container in proximity to the fluidic barrier by an optical imaging system.

3. A method as defined by claim 1, wherein the flotation solution is zinc sulfate.

4. A method as defined by claim 1, wherein the barrier-forming fluid is oleyl alcohol.

5. A method as defined by claim 1, wherein the barrier-forming fluid is a sucrose solution.

6. A method for separating particles from a sample of matter and concentrating the particles in a predefined area of a collection container, which comprises the steps of:

mixing in the collection container the sample of matter containing the particles with a flotation solution having a predetermined specific gravity such that the particles are suspended in the flotation solution, the collection container including walls defining an interior cavity for holding the flotation solution having the particles suspended therein;

adding a barrier-forming fluid to the interior cavity of the collection container such that the barrier-forming fluid resides on top of the flotation solution, the barrier-forming fluid being immiscible with the flotation solution and having a specific gravity which is less than the specific gravity of the flotation solution and specific gravities of the particles suspended in the flotation solution, the barrier-forming fluid being in contact with the flotation solution at an interface between the flotation solution and the barrier-forming fluid, the flotation solution and the immiscible barrier-forming fluid forming a fluidic barrier within the interior cavity of the collection container at the interface between the flotation solution and the barrier-forming fluid; and centrifuging the collection container holding flotation solution having the particles suspended therein and the barrier-forming fluid within the interior cavity of the collection container so that particles suspended in the flotation solution having specific gravities which are less than the specific gravity of the flotation solution separate therefrom and move in the interior cavity of the collection container to form a concentrated quantity of separated particles accumulating at a location within the interior cavity of the collection container in proximity to the fluidic barrier.

7. A method as defined by claim 6, which further comprises the step of: optically imaging the concentrated quantity of separated particles accumulating at the location within the interior cavity of the collection container in proximity to the fluidic barrier by an optical imaging system.

8. A method as defined by claim 6, wherein the flotation solution is zinc sulfate.

9. A method as defined by claim 6, wherein the barrier-forming fluid is oleyl alcohol.

10. A method as defined by claim 6, wherein the barrier-forming fluid is a sucrose solution.

* * * * *